US012576266B2

(12) United States Patent
Clawson et al.

(10) Patent No.: US 12,576,266 B2
(45) Date of Patent: Mar. 17, 2026

(54) CRANIAL IMPLANT WITH WIRE MANAGEMENT STRUCTURE

(71) Applicant: Longeviti Neuro Solutions, Inc., Baltimore, MD (US)

(72) Inventors: Corbin Clawson, Hampstead, MD (US); Jimmy Shah, Philadelphia, PA (US); Wilbert Pierce, Baltimore, MD (US)

(73) Assignee: Longeviti Neuro Solutions, Inc., Baltimore, MD (US)

( * ) Notice: Subject to any disclaimer, the term of this patent is extended or adjusted under 35 U.S.C. 154(b) by 716 days.

(21) Appl. No.: 18/050,345

(22) Filed: Oct. 27, 2022

(65) Prior Publication Data

US 2023/0130616 A1　　Apr. 27, 2023

Related U.S. Application Data

(60) Provisional application No. 63/263,121, filed on Oct. 27, 2021.

(51) Int. Cl.
　　*A61N 1/00*　　(2006.01)
　　*A61N 1/05*　　(2006.01)

(52) U.S. Cl.
　　CPC ................................. *A61N 1/0539* (2013.01)

(58) Field of Classification Search
　　None
　　See application file for complete search history.

(56) References Cited

U.S. PATENT DOCUMENTS

| | | |
|---|---|---|
| 6,016,449 A | 1/2000 | Fischell et al. |
| 6,354,299 B1 | 3/2002 | Fischell et al. |
| 6,427,086 B1 | 7/2002 | Fischell et al. |
| 6,591,138 B1 | 7/2003 | Fischell et al. |
| 7,004,948 B1 * | 2/2006 | Pianca ............... A61B 17/3462 |
| | | 607/116 |
| 7,242,982 B2 | 7/2007 | Singhal et al. |
| 7,263,401 B2 | 8/2007 | Scott et al. |
| 7,346,391 B1 | 3/2008 | Osorio et al. |
| 7,529,586 B2 | 5/2009 | Wahlstrand et al. |
| 7,548,775 B2 | 6/2009 | Kipke et al. |
| 7,596,399 B2 | 9/2009 | Singhal et al. |

(Continued)

FOREIGN PATENT DOCUMENTS

| | | |
|---|---|---|
| EP | 3020450 A1 | 5/2016 |
| WO | 2019104187 A1 | 5/2019 |

*Primary Examiner* — Niketa Patel
*Assistant Examiner* — Anant A Gupta
(74) *Attorney, Agent, or Firm* — Welsh Flaxman & Gitler LLC

(57) ABSTRACT

A low-profile cranial device is adapted for covering and protecting electrical leads. The cranial device includes a static cranial implant shaped and dimensioned for housing a functional neurosurgical implant including electrical leads. The static cranial implant includes an outer first surface along an exterior side of the static cranial implant, an inner second surface along an interior side of the static cranial implant, and a peripheral wall extending between the outer first surface and the inner second surface. A cavity is formed along the outer first surface of the static cranial implant, the cavity being shaped and dimensioned to house the functional neurosurgical implant in a manner allowing the electrical leads to be wound up to store excess electrical lead length.

17 Claims, 20 Drawing Sheets

(56) References Cited

U.S. PATENT DOCUMENTS

| | | | |
|---|---|---|---|
| 7,596,408 B2 | 9/2009 | Singhal et al. | |
| 7,647,097 B2 | 1/2010 | Flaherty et al. | |
| 7,848,817 B2 | 12/2010 | Janzig et al. | |
| 8,397,732 B2 | 3/2013 | Singhal et al. | |
| 9,014,810 B2 | 4/2015 | Sauter-Starace et al. | |
| 9,084,901 B2 | 7/2015 | Wahlstrand | |
| 9,421,363 B2 | 8/2016 | Krahl et al. | |
| 11,331,474 B2 | 5/2022 | Rabinovitz | |
| 2005/0015128 A1* | 1/2005 | Rezai | A61N 1/0539 |
| | | | 600/378 |
| 2013/0304216 A1 | 11/2013 | Paspa et al. | |
| 2017/0049398 A1 | 2/2017 | Hirata et al. | |
| 2019/0209328 A1* | 7/2019 | Christopher | A61N 1/0539 |
| 2019/0308025 A1* | 10/2019 | Bauer | A61N 1/0534 |
| 2021/0121088 A1 | 4/2021 | Christopher | |
| 2022/0387791 A1 | 12/2022 | Bakker | |

* cited by examiner

CRANIAL IMPLANT WITH WIRE MANAGEMENT STRUCTURE

CROSS REFERENCE TO RELATED APPLICATION

This application claims the benefit of U.S. Provisional Patent Application Ser. No. 63/263,121, entitled "CRANIAL IMPLANT WITH WIRE MANAGEMENT STRUCTURE," filed Oct. 27, 2021, which is incorporated herein by reference.

BACKGROUND OF THE INVENTION

1. Field of the Invention

The present invention relates to a wire management structure for a cranial implant.

2. Description of the Related Art

Surgeons regularly deal with excess lead length when implanting medical devices with electrical leads. Sufficient lead length is required to allow proper placement of electrodes in a variety of anatomical locations and to account for a variety of anatomical dimensions from patient to patient. However, and due to the need for suitable electrical connections, the lead length commonly cannot be altered after manufacturing. Therefore, medical devices are commonly manufactured with an excess lead length that must be dealt with by the surgeon.

A common approach to dealing with excess lead length during cranial procedures is to coil the leads and place the coil between the skin and cranium for devices placed on or within the cranial space. This may lead to palpable or visible bumps under the patient's scalp. This also requires additional manipulation of the patient's anatomy and the leads by the surgeon during placement.

A need, therefore, exists for medical devices addressing this problem.

SUMMARY OF THE INVENTION

According to one aspect a low-profile cranial device adapted for covering and protecting electrical leads includes a static cranial implant shaped and dimensioned for housing a functional neurosurgical implant including electrical leads. The static cranial implant includes an outer first surface along an exterior side of the static cranial implant, an inner second surface along an interior side of the static cranial implant, and a peripheral wall extending between the outer first surface and the inner second surface. A cavity is formed along the outer first surface of the static cranial implant. The cavity is shaped and dimensioned to house the functional neurosurgical implant in a manner allowing the electrical leads to be wound up to store excess electrical lead length.

In some embodiments the static cranial implant is shaped and dimensioned for positioning within an intercranial space.

In some embodiments the static cranial implant is shaped and dimensioned for positioning between a skull and a scalp.

In some embodiments the low-profile cranial device includes a functional neurosurgical implant.

In some embodiments the functional neurosurgical implant is generally disk shaped and includes an upper surface, a lower surface, and a perimeter sidewall extending between the upper surface and the lower surface along the edge of the functional neurosurgical implant.

In some embodiments the upper surface includes a textured portion for gripping when it is desired to rotate the functional neurosurgical implant and the lower surface includes a base surface shaped and dimensioned to sit upon the base of the cavity.

In some embodiments the static cranial implant includes an annular circumferential recess along a circumferential interior wall of the cavity.

In some embodiments the outer first surface and inner second surface of the static cranial implant are curved in a superior to inferior direction, a posterior to anterior direction, and a medial to lateral direction.

In some embodiments the static cranial implant has a thickness between the outer first surface and the inner second surface of between 1 millimeter to 25 millimeters.

In some embodiments the static cranial implant has a thickness of 1 millimeter to 12 millimeters.

In some embodiments the cranial implant is fabricated from PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs.

In some embodiments the static cranial implant is made of clear PMMA.

In some embodiments the static cranial implant allows for transmission of ultrasound waves.

In some embodiments the cavity is circular and is formed along the outer first surface of the static cranial implant.

In some embodiments the cavity is defined by a circular base and a circumferential interior wall formed along the outer first surface of the static cranial implant. The circumferential interior wall extends upwardly from the base to the exterior of the outer first surface of the static cranial implant.

In some embodiments the circumferential interior wall extends upwardly from the base to a point where it meets the outer first surface.

In some embodiments the low-profile cranial device includes an annular circumferential recess formed along the circumferential interior wall of the cavity.

In some embodiments the annular circumferential recess is defined by a lower wall, an upper wall, and a connecting wall extending between the lower wall and the upper wall. The connecting wall of the annular circumferential recess is separated from the circumferential interior wall of the cavity by the upper and lower walls.

In some embodiments the low-profile cranial device includes radially extending slots formed along the periphery of the static cranial implant. The slots connect the interior of the annular circumferential recess to the exterior of the static cranial implant at the periphery of the static cranial implant.

In some embodiments passage of the electrical leads to exterior locations is further facilitated by a guiding channel formed in the outer first surface of the static cranial implant such that the guiding channel is in alignment with the slots formed in the periphery of the static cranial implant.

In some embodiments the outer first surface includes a plurality of radially extending flanges that extends outwardly of the peripheral wall of the static cranial implant.

In some embodiments each of the flanges includes an upper surface that defines an exterior of the outer first surface and a lower surface that ultimately is positioned upon a cranium when the circular base and a circumferential interior wall are positioned in a resected portion of the cranium.

In some embodiments the low-profile cranial device includes a cover member in which the functional neurosurgical implant is positioned.

In some embodiments the static cranial implant includes an annular circumferential recess along a circumferential interior wall of the cavity.

In some embodiments the outer first surface and inner second surface of the static cranial implant are curved in a superior to inferior direction, a posterior to anterior direction, and a medial to lateral direction.

In some embodiments the cavity is defined by a circular base and a circumferential interior wall formed along the outer first surface of the static cranial implant, and the circumferential interior wall extends upwardly from the base to the exterior of the outer first surface of the static cranial implant to a point where it meets the outer first surface, and an annular upstanding wall is formed internally of the circumferential interior wall, the annular upstanding wall extending upwardly from the base to a height slightly lower than that of the circumferential interior wall.

In some embodiments the annular upstanding wall is positioned within the circumferential interior wall, and the circumferential interior wall defines a diameter that is larger than the diameter defined by the annular upstanding wall.

In some embodiments the annular upstanding wall is formed with multiple segments.

In some embodiments a cover member is further provided for housing the functional neurosurgical implant, and the cover member is shaped and dimensioned for positioning within the cavity and for rotation of both the cover member and the functional neurosurgical implant in a controlled manner.

In accordance with another aspect a low-profile cranial device adapted for covering and protecting electrical leads includes a static cranial implant shaped and dimensioned for housing a functional neurosurgical implant. The static cranial implant includes an outer first surface along an exterior side of the static cranial implant, an inner second surface along an interior side of the static cranial implant, and a peripheral wall extending between the outer first surface and the inner second surface. A cavity is formed along the outer first surface of the static cranial implant. The device also includes a central rotation member shaped and dimensioned for positioning within the cavity and for rotation of the central rotation member.

In some embodiments the static cranial implant is shaped and dimensioned for positioning between a skull and a scalp.

In some embodiments the cavity is defined by a circular base and a circumferential interior wall formed along the outer first surface of the static cranial implant, and the circumferential interior wall extends upwardly from the base to an exterior of the outer first surface of the static cranial implant to a point where it meets the outer first surface, and an annular upstanding wall is formed internally of the circumferential interior wall, the annular upstanding wall extending upwardly from the base to a height slightly lower than that of the circumferential interior wall.

In some embodiments the annular upstanding wall is positioned within the circumferential interior wall, and the circumferential interior wall defines a diameter that is larger than the diameter defined by the annular upstanding wall.

In some embodiments the annular upstanding wall is formed with multiple segments.

In some embodiments the low-profile cranial device includes radially extending slots formed along the periphery of the static cranial implant, the slots connect to an exterior of the static cranial implant at the periphery of the static cranial implant.

In some embodiments passage of the electrical leads to exterior locations is further facilitated by a guiding channel formed in the outer first surface of the static cranial implant such that the guiding channel is in alignment with the slots formed in the periphery of the static cranial implant.

In some embodiments the outer first surface includes a plurality of radially extending flanges that extend outwardly of the peripheral wall of the static cranial implant.

In some embodiments each of the flanges includes an upper surface that defines an exterior of the outer first surface and a lower surface that ultimately is positioned upon a cranium when the circular base and a circumferential interior wall are positioned in a resected portion of the cranium.

In some embodiments the central rotation member holds the electrical lead and controls take-up of the electrical lead.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
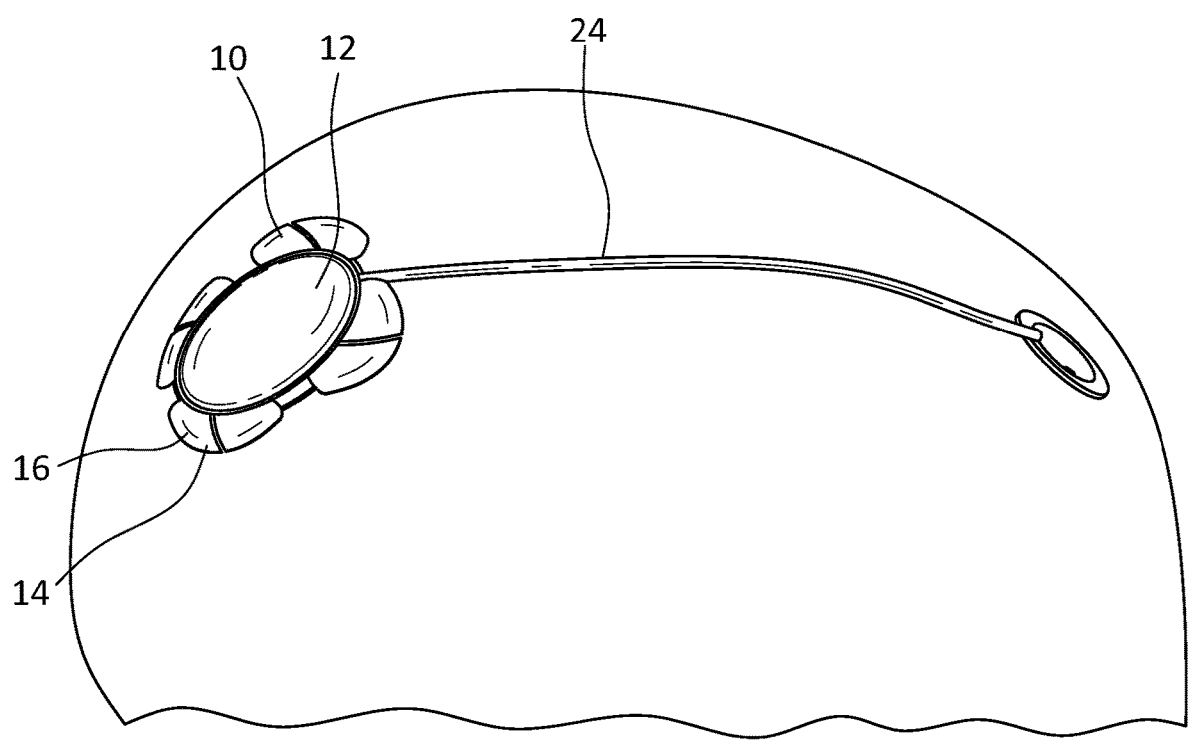
FIG. 1 is a perspective view of a first embodiment of a cranial device with a wire management structure in use.
Figure 2:
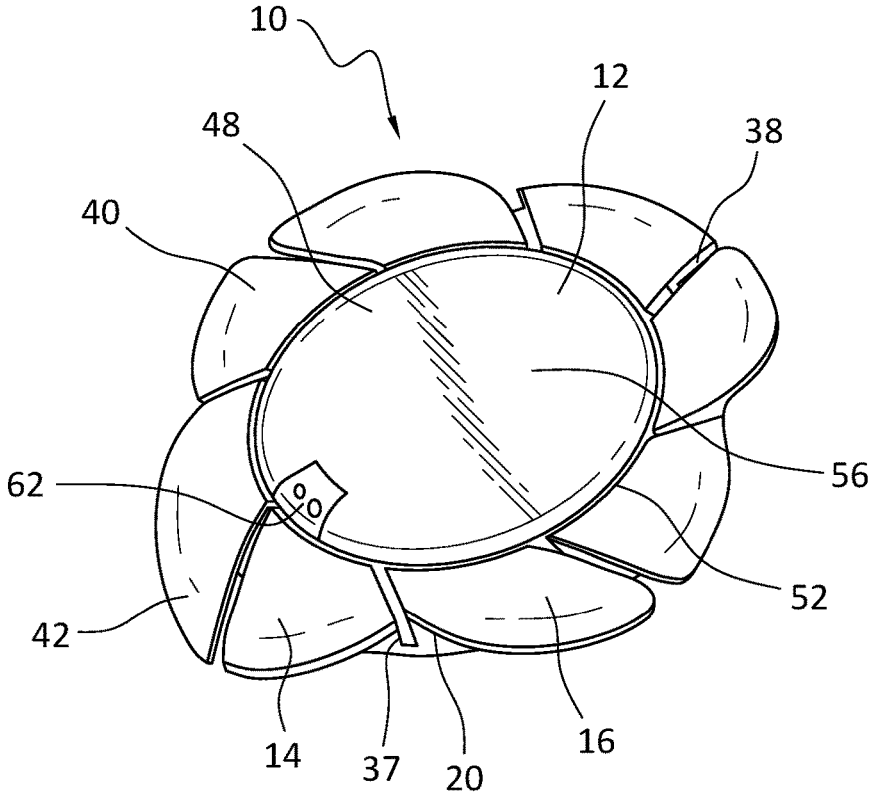
FIG. 2 is a perspective view of the cranial device shown in FIG. 1.
Figure 3:
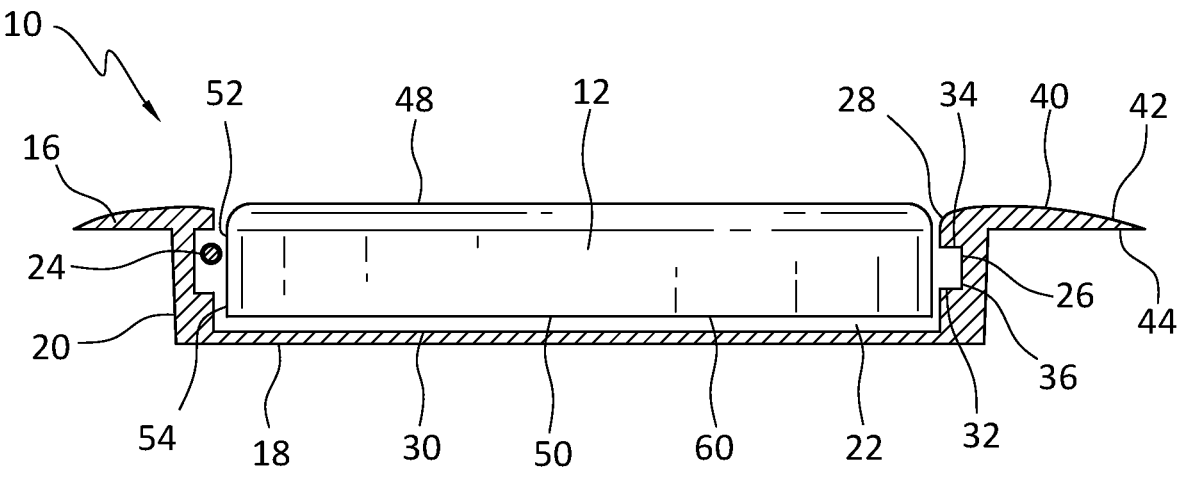
FIG. 3 is a cross sectional view of the cranial device shown in FIG. 1.
Figure 4:
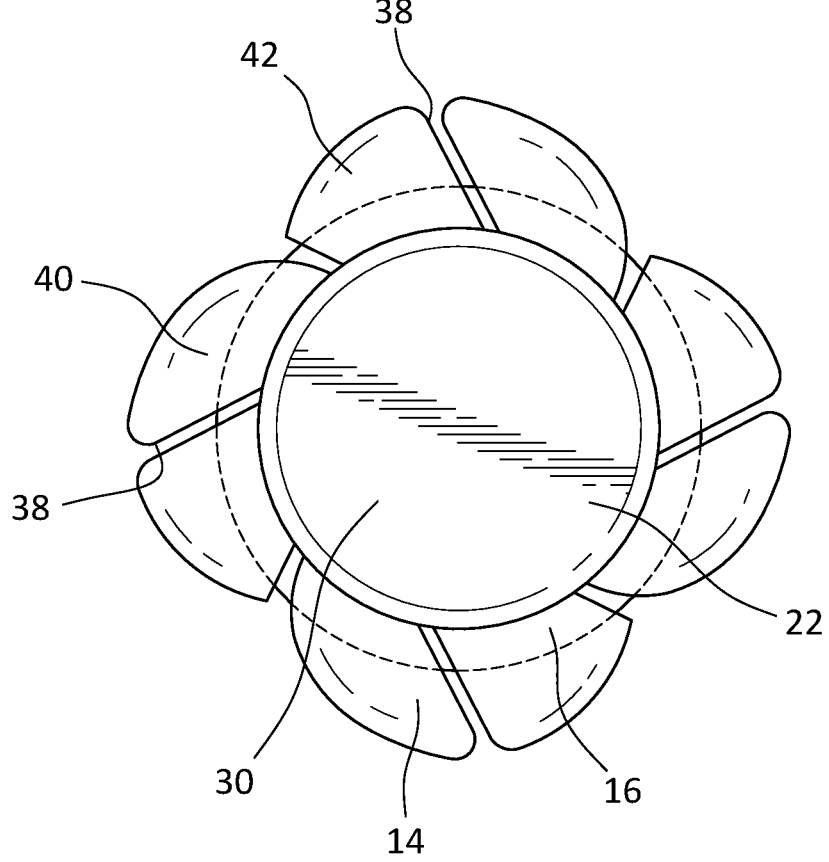
FIG. 4 is a top plan view of the cranial device shown in FIG. 1.
Figure 5:
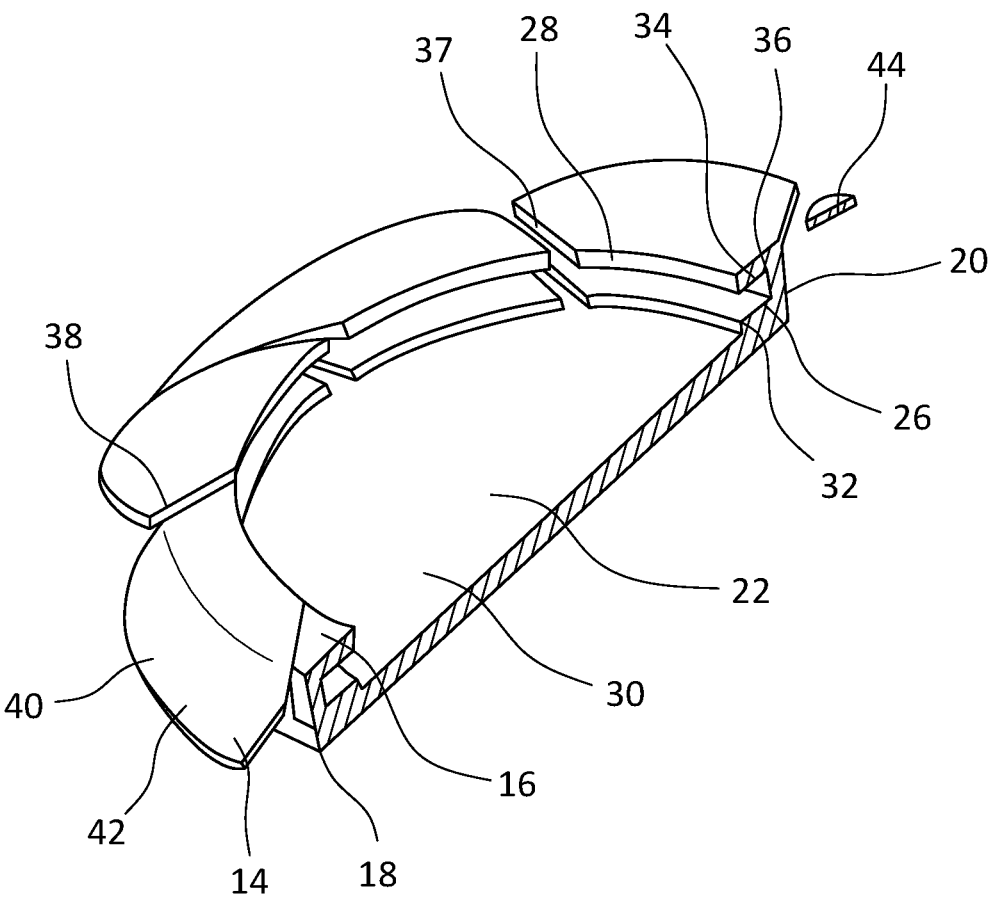
FIG. 5 is a perspective sectional view of the cranial implant of the cranial device shown in FIG. 1.
Figure 6:
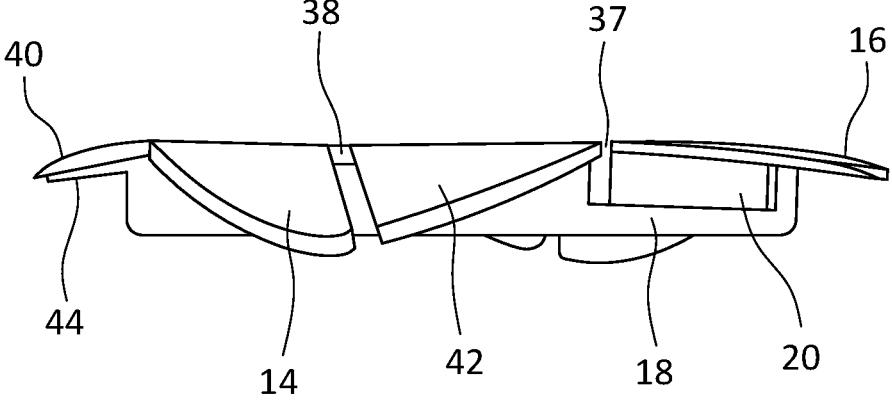
FIG. 6 is a side view of the cranial implant of the cranial device shown in FIG. 1.
Figure 7:
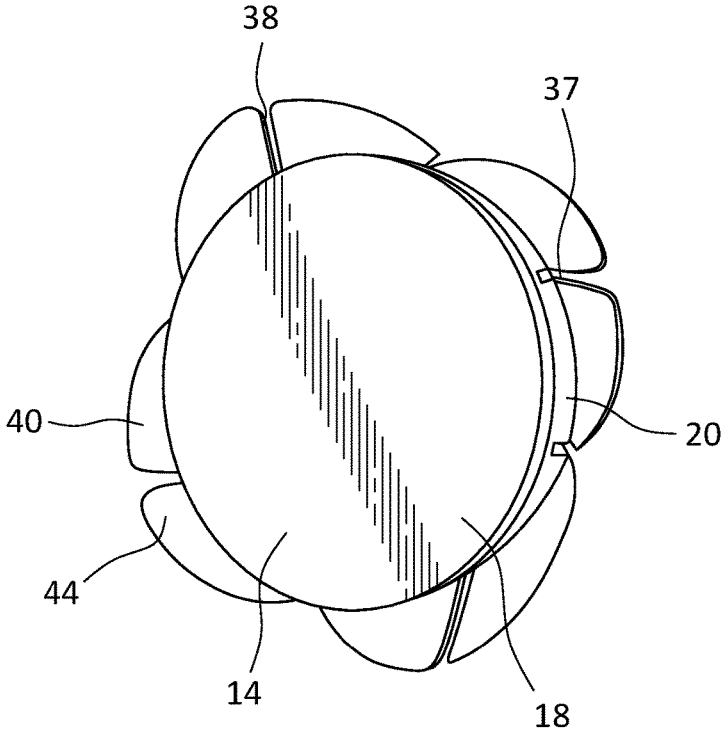
FIG. 7 is a bottom perspective view of the cranial implant of the cranial device shown in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 8, a low-profile cranial device 10 is disclosed. As will be appreciated based upon the following disclosure, the low-profile cranial device 10 provides an easy and intuitive way to store excess electrical lead length of a functional neurosurgical implant 12 while also housing the functional neurosurgical implant 12 attached to the electrical leads 24. As will be appreciated based upon the following disclosure, the present low-profile cranial device 10 simplifies the process of dealing with excess lead length by allowing the surgeon to spool the excess lead length around the device in an easy and intuitive way. The present low-profile cranial device 10 stores the leads within a protected space that reduces the visible or palpable bumps of the leads under the scalp. The present low-profile cranial device 10 also protects the leads from damage or breakage by storing the excess length within a protected area.

Through the application of rotational motion of the functional neurosurgical implant 12, the low-profile cranial device 10 provides a solution to the problem of having to manage excess electrical lead length. The present low-profile cranial device 10 covers the electrical leads 24 and thereby protects the electrical leads 24 from damage due to external forces. The low-profile cranial device 10 can be adapted to house a variety of functional neurosurgical implants 12 with a range of diameters.

The low-profile cranial device 10 is generally composed of a static cranial implant 14 and a functional neurosurgical implant 12. As will be appreciated based upon the following disclosure, the static cranial implant 14 is shaped and dimensioned to house the functional neurosurgical implant 12, with both being implanted within the cranium of a patient.

The static cranial implant 14 includes an outer (commonly convex) first surface 16 along the exterior side of the static cranial implant 14, an inner (commonly concave) second surface 18 along the interior side of the static cranial implant 14, and a peripheral wall 20 extending between the outer first surface 16 and the inner second surface 18. The static cranial implant 14 is shaped and dimensioned for engagement with the skull of the patient upon implantation in a manner well known to those skilled in the field of neurosurgical procedures.

The outer first surface 16 and inner second surface 18 of the static cranial implant 14 are preferably curved in a superior to inferior direction, a posterior to anterior direction, and a medial to lateral direction. As will be appreciated based upon the following disclosure, the outer first surface 16 is substantially annular as the static cranial implant 14 includes a cavity 22 formed therein. The inner second surface 18 is a substantially continuous surface and ultimately defines the bottom wall of the static cranial implant 14.

In accordance with a preferred embodiment, the static cranial implant 14 has a preselected thickness, that is, the distance between the outer first surface 16 and the inner second surface 18, approximating the thickness of the cranium and not exceeding the space between the inner surface of the scalp and the outer surface of the dura, for example, in the range of around 1 millimeter to 25 millimeters (with areas of strategic bulking and/or thinning) and depending upon the strength of the materials used in the construction of the static cranial implant 14. Preferably, the static cranial implant 14 will have a thickness of 1 millimeter to 12 millimeters. As briefly mentioned above, the static cranial implant 14 also includes a cavity 22 formed along the outer first surface 16.

In accordance with a preferred embodiment, the customized cranial implant 14 is fabricated from a wide array of commonly available biomaterials including, but not limited to, clear and/or opaque PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs. In accordance with one embodiment, the static cranial implant 14 is made of clear PMMA since it is fully lucent and transparent. As will be explained below in greater detail, clear PMMA also allows for the critical transmission of vital imaging with minimal distortion, such as ultrasound waves for brain pathology detection, and wireless signal communication (i.e., electroencephalography or ECOG)—essential for various neuromodulation devices such as NeuroPace®. Another clear material that may be readily used in accordance with the present invention is cubic zirconium. While clear material is disclosed in accordance with a preferred embodiment, it is appreciated the underlying concepts of the present invention may be achieved through the utilization of opaque static cranial implants.

As discussed above, the functional neurosurgical implant 12 includes electrical leads 24, and the static cranial implant 14 is constructed to hold the functional neurosurgical implant 12 in a manner allowing the electrical leads 24 to be wound up to store excess electrical lead length. This is achieved by forming an annular circumferential recess 26 along the circumferential interior wall 28 of the cavity 22 in which the functional neurosurgical implant 12 is housed.

The cavity 22 of the static cranial implant 14 is circular and is formed along the outer first surface 16 of the static cranial implant 14. The cavity 22 is defined by a circular base 30 and a circumferential interior wall 28 formed along the outer first surface 16 of the static cranial implant 14. The circumferential interior wall 28 extends upwardly from the base 30 to the exterior of the outer first surface 16 of the static cranial implant 14. The circumferential interior wall 28 extends upwardly from the base 30 to a point where it meets the outer first surface 16.

The annular circumferential recess 26 mentioned above is formed along the circumferential interior wall 28 of the cavity 22. As such, the annular circumferential recess 26 is defined by a lower wall 32, an upper wall 34, and a connecting wall 36 extending between the lower wall 32 and the upper wall 34. The connecting wall 36 of the annular circumferential recess 26 is separated from the circumferential interior wall 28 of the cavity 22 by the length of the upper and lower walls 34, 32.

Passage of the electrical leads 24 to exterior locations as desired is facilitated by the provision of radially extending slots 37 formed along the periphery of the static cranial implant 14. The slots 37 connect the interior of the annular circumferential recess 26 to the exterior of the static cranial implant 14 at the periphery of the static cranial implant 14. Passage of the electrical leads 24 to exterior locations is further facilitated by the provision of a guiding channel 38 formed in the outer first surface 16 of the static cranial implant 14 such that the guiding channel 38 is in alignment with the slots 37 formed in the periphery of the static cranial implant 14.

In particular, the outer first surface 16 includes a plurality of radially extending flanges 40 that extend outwardly of the peripheral wall of the static cranial implant 14. As such, each of the flanges 40 includes an upper surface 42 that defines the exterior of the outer first surface 16 of the static cranial implant 14 and a lower surface 44 that ultimately is positioned upon the cranium when the circular base 30 and the circumferential interior wall 28 are positioned in the resected portion of the cranium created during the installation process.

The functional neurosurgical implant 12 is shaped and dimensioned for positioning within the cavity 22 and for rotation in a controlled manner. The functional neurosurgical implant 12 is generally disk shaped and includes an upper surface 48, a lower surface 50, and a perimeter sidewall 52 extending between the upper surface 48 and the lower surface 50 along an edge 54 of the functional neurosurgical implant 12. The upper surface 48 includes a textured portion 56 for gripping when it is desired to rotate the functional neurosurgical implant 12. The lower surface 50 includes a base surface 60 shaped and dimensioned to sit upon the base 30 of the cavity 22.

The functional neurosurgical implant 12 of the present invention is selected from a variety of FDA-approved and experimental options for electrical, optical, mechanical, medicinal, and other treatment/monitoring devices designed for long term invasive treatment and/or disease-monitoring of patients requiring such attention. These functional neurosurgical implants are known devices manufactured by various vendors within the neurosurgical industry and have known, unmodifiable dimensions that may be considered when modifying the static cranial implant to optimize surgical results by minimizing abnormal shapes, visible contours, and/or craniofacial deformities.

Based upon the functional neurosurgical implant 12 used in conjunction with the present invention, the functional neurosurgical implant 12 may be useful in the treatment of various patient conditions such as epilepsy, movement disorders, chronic pain, spasticity, cerebral palsy, multiple sclerosis, spinal cord injury, traumatic brain injury, attention-deficit/hyperactivity disorder, autism, etc. There is also potential to obtain supra-normal levels of brain function in both military and civilian situations. Furthermore, the incorporation of imaging devices within cranial implants could provide ongoing tumor bed monitoring for early detection of disease recurrence.

With this in mind, the term "functional neurosurgical implant" is meant to refer to any therapeutic hardware or compositions including, but not limited to, medicines to treat any patient-specific illness, or electronic, mechanical, imaging modality and/or electro-mechanical device to remotely monitor (e.g., via Wi-Fi connectivity) or intervene in any specific neurologic illness, including imaging, monitoring, electrostimulation, radiation therapy, and polarized light/laser neuronal modulation devices. The term "functional" denotes the fact that these implants provide the low-profile cranial device 10 with the ability to function as more than a safe custom-shaped skull replacement by providing various functionalities, for example, local drug delivery, monitoring (such as brain monitoring), or local electric stimulation to the patient.

In practice, the low-profile cranial device 10 is installed in a resected portion of the cranium using conventional installation techniques. In one embodiment, a craniotomy is performed with a diameter equal to the diameter of the static cranial implant 14 as defined by the circumferential interior wall 28. The static cranial implant 14, in particular, the circumferential interior wall 28, sits within the craniotomy, thus reducing the overall profile of the functional neurosurgical implant 12 to be held within the static cranial implant 14. The flanges 40 defining the outer first surface 16 of the static cranial implant 14 lie on top of the cranium and allow fixation of the low-profile cranial device 10 using screws, plates, bioadhesives, or other traditional or novel methods. The channel 38 formed within the flange allows the electrical leads 24 to access the annular circumferential recess 26 for electrical lead spooling.

Figure 8:
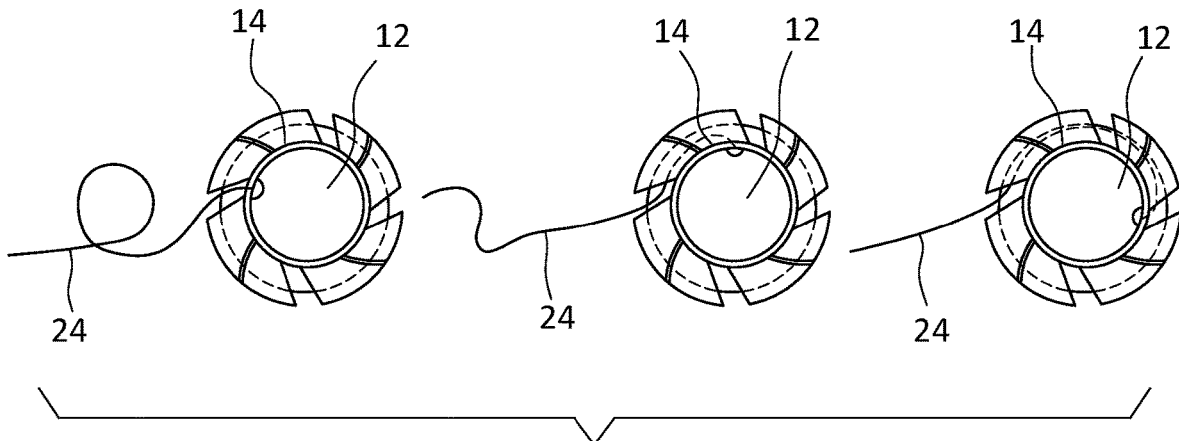
FIG. 8 is a schematic showing the sequence of steps in the operation of the cranial device shown in FIG. 1.
Figure 9:
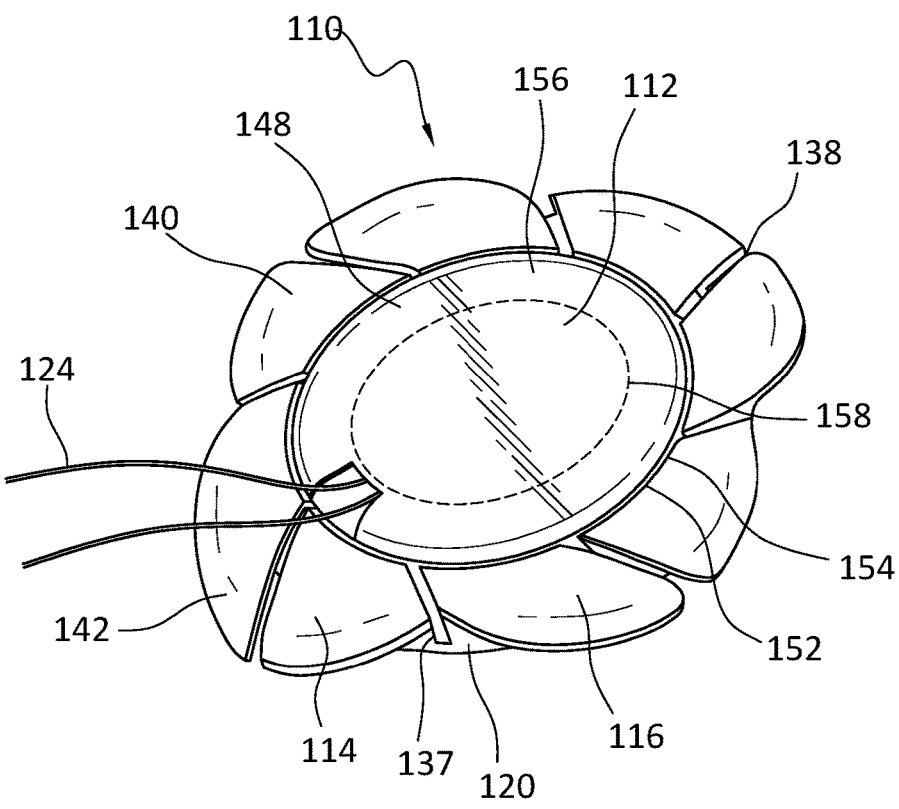
FIG. 9 is a perspective view of a second embodiment of a cranial device with a wire management structure.
Figure 10:
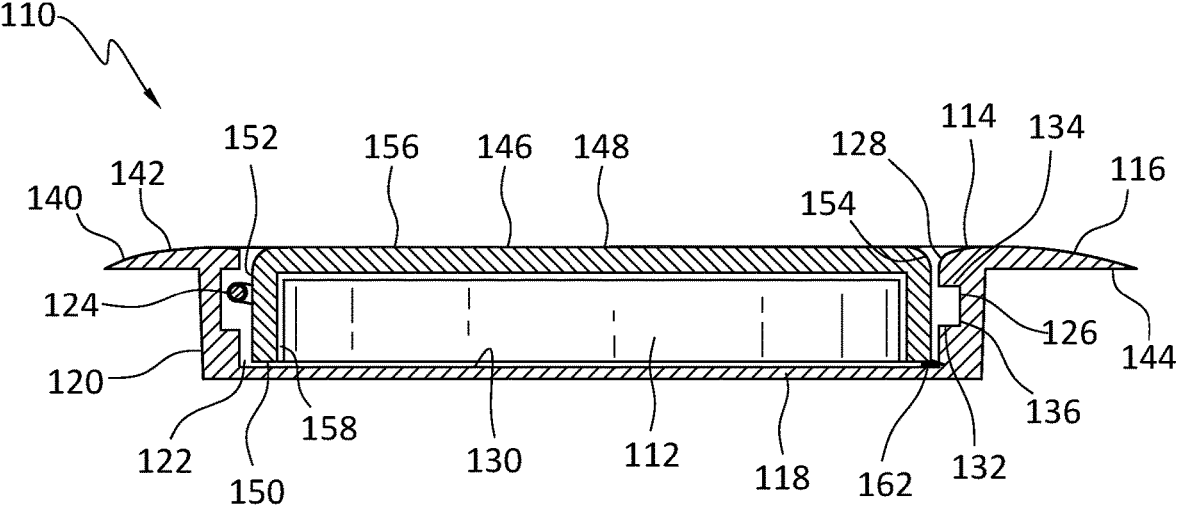
FIG. 10 is a cross sectional view of the cranial device shown in FIG. 9.
Figures 11, 12:
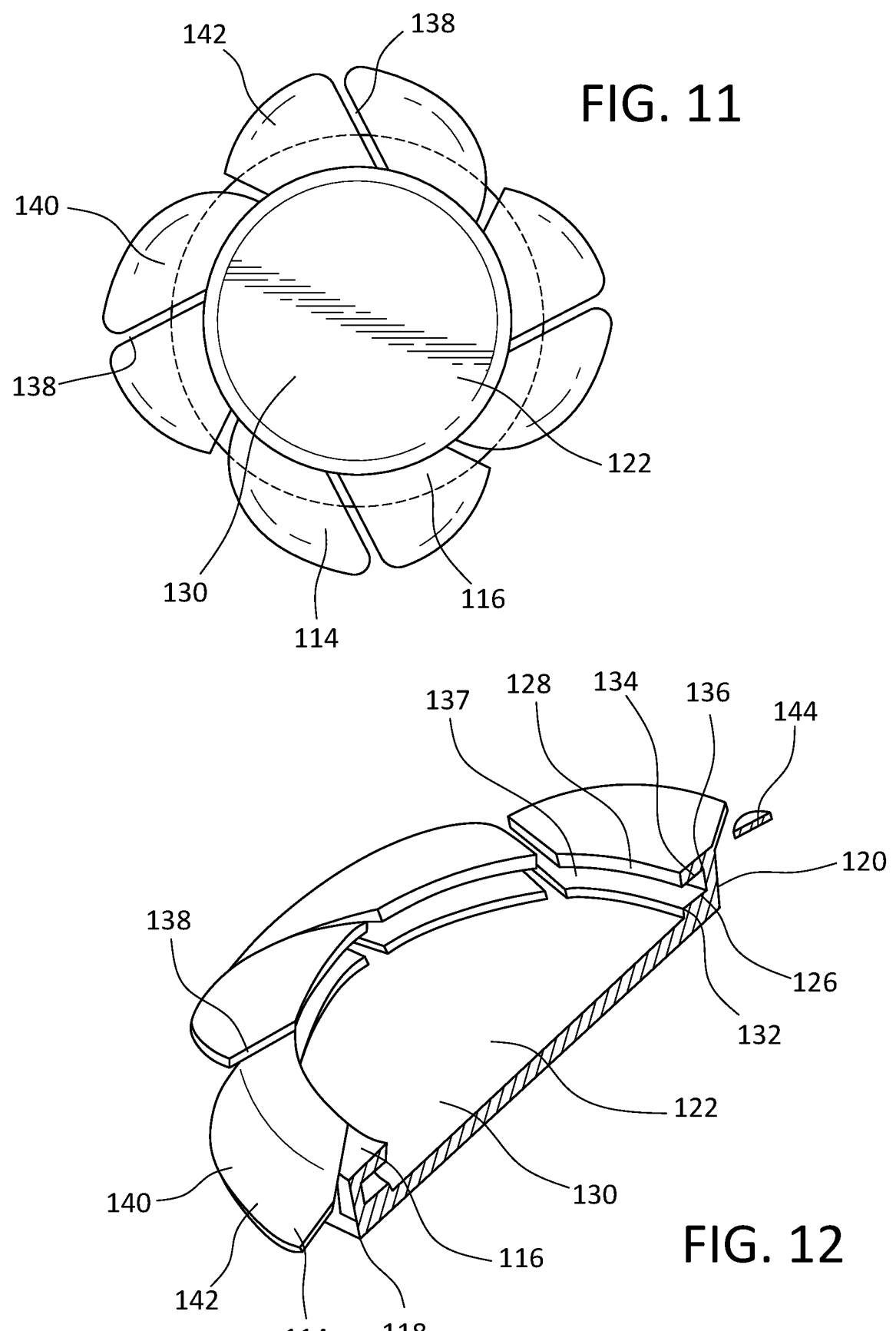
FIG. 11 is a top plan view of the cranial device shown in FIG. 9.
FIG. 12 is a perspective sectional view of the cranial implant of the cranial device shown in FIG. 9.
Figure 13:
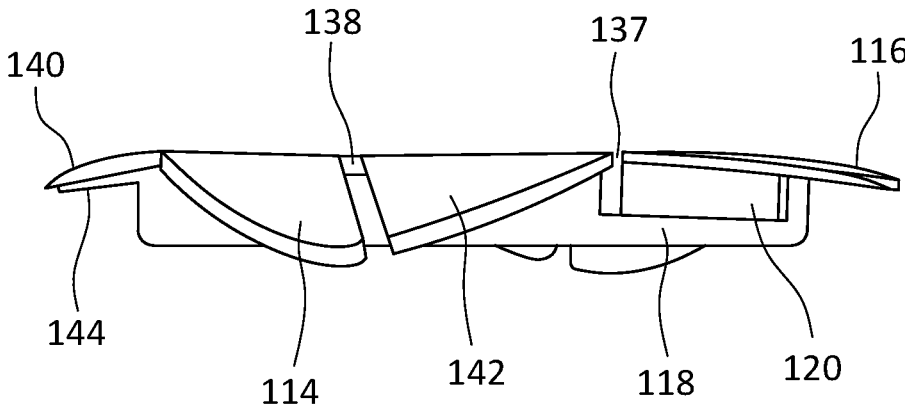
FIG. 13 is a side view of the cranial implant of the cranial device shown in FIG. 9.
Figure 14:
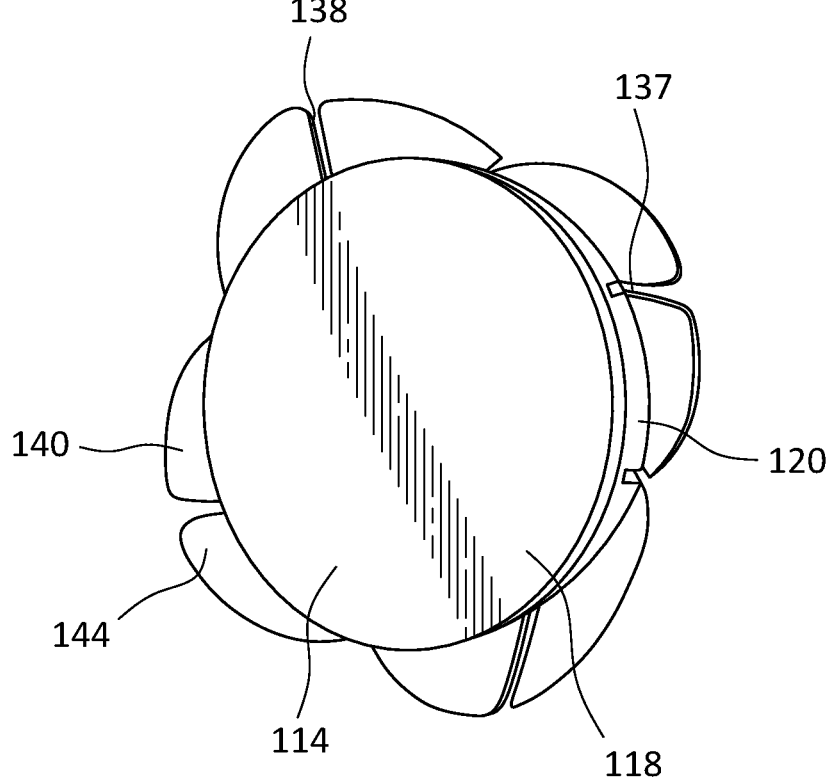
FIG. 14 is a bottom perspective view of the cranial implant of the cranial device shown in FIG. 9.
Figure 15:
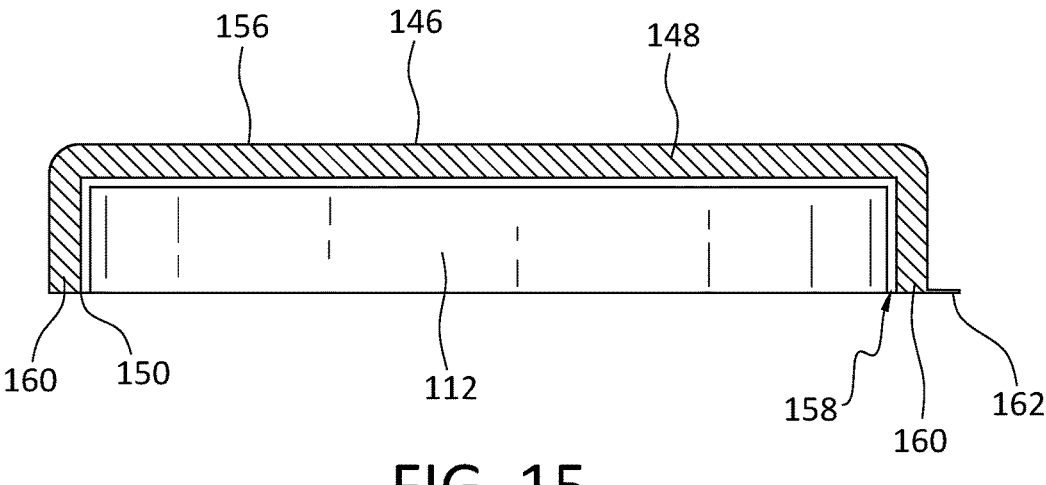
FIG. 15 is a cross sectional view showing the cover member housing the functional neurosurgical implant of the cranial device shown in FIG. 9.

With low-profile cranial device 10 installed in a resected portion of the cranium, the electrical leads 24 of the functional neurosurgical implant 12 are secured to electrical connection members 62 within the upper surface 48 of the functional neurosurgical implant 12 for electrical connection. The functional neurosurgical implant 12 is rotated (for example, in a clockwise direction as shown in FIG. 8) causing excess electrical lead length to spool into the annular circumferential recess 26 formed along the circumferential interior wall 28 of the cavity 22 formed within the static cranial implant 14. The user can continue to rotate the functional neurosurgical implant 12 until the desired amount of excess electrical lead length is spooled within the channel.

It is appreciated that the geometry of the low-profile cranial device 10 is such that there are no features between the outer surface of the rotating portion of the functional neurosurgical implant 12 and the annular circumferential recess 26 where the electrical leads 24 are spooled or stored.

This allows the free rotation of the functional neurosurgical implant 12 and simultaneously allows the electrical leads 24 to fill the channel.

While the present disclosure provides that the functional neurosurgical implant is rotated to spool excess electrical lead length after installation of the static cranial implant within a resected portion of the cranium, the electrical lead length may be spooled prior to installation where so desired.

Considering the excess electrical lead length is intended to gather and be stored within the circumferential recess, the circumferential recess may be provided with features that prevent the spooled electrical leads from exiting the channel or area, such as lips, overhangs, covers, or other such guiding features. The low-profile cranial device may also be provided with an inlet channel (in addition to the channel already discussed above) to allow the electrical leads to access the circumferential recess from areas distal to the static cranial implant. The static cranial implant may also be provided with tabs or other features to facilitate fixation to existing anatomical features.

Referring to FIGS. 9 to 16, another embodiment of a low-profile cranial device 110 is disclosed. In accordance with this embodiment, the functional neurosurgical implant 112 is positioned within a cover member 146 that is then positioned within the cavity 122 of the static cranial implant 114. As with the prior embodiment, the low-profile cranial device 110 provides an easy and intuitive way to store the excess electrical lead length of a functional neurosurgical implant 112 while also housing a functional neurosurgical implant 112 attached to the electrical leads 124. Through the application of a simple rotating motion of the cover member 146 and the functional neurosurgical implant 112, the present low-profile cranial device 110 allows for convenient management of excess electrical lead length. The present low-profile cranial device 110 covers the electrical leads 124 and thereby protects the electrical leads 124 from damage due to external forces. The low-profile cranial device 110 can house a variety of functional neurosurgical implants 112 with a range of diameters.

The static cranial implant 114 includes an outer (commonly convex) first surface 116 along the exterior side of the static cranial implant 114, an inner (commonly concave) second surface 118 along the interior side of the static cranial implant 114, and a peripheral wall 120 extending between the outer first surface 116 and the inner second surface 118. The static cranial implant 114 is shaped and dimensioned for engagement with the skull of the patient upon implantation in a manner well known to those skilled in the field of neurosurgical procedures.

The outer first surface 116 and inner second surface 118 of the static cranial implant 114 are preferably curved in a superior to inferior direction, a posterior to anterior direction, and a medial to lateral direction. The outer first surface 116 is substantially annular as the static cranial implant 114 includes a cavity 122 formed therein. The inner second surface 118 is a substantially continuous surface and ultimately defines the bottom wall of the static cranial implant 114.

The static cranial implant 114 has a preselected thickness, that is, the distance between the outer first surface 116 and the inner second surface 118, approximating the thickness of the cranium and not exceeding the space between the inner surface of the scalp and the outer surface of the dura, for example, in the range of around 1 millimeter to 25 millimeters (with areas of strategic bulking and/or thinning) and depending upon the strength of the materials used in the construction of the static cranial implant 114. Preferably, the static cranial implant 114 has a thickness of 1 millimeter to 12 millimeters.

As briefly mentioned above, the static cranial implant 114 also includes a cavity 122 formed along the outer first surface 116. The cranial implant 114 is fabricated from a wide array of commonly available biomaterials as discussed above with regard to the embodiment disclosed with reference to FIGS. 1 to 8.

The functional neurosurgical implant 112 includes electrical leads 124, and the static cranial implant 114 is constructed to hold the functional neurosurgical implant 112 in a manner allowing the electrical leads 124 to be wound up to store excess electrical lead length. This is achieved by forming an annular circumferential recess 126 along the circumferential interior wall 128 of the cavity 122 in which the functional neurosurgical implant 112 is housed.

In particular, the cavity 122 of the static cranial implant 114 is circular and is formed along the outer first surface 116 of the static cranial implant 114. The cavity 122 is defined by a circular base 130 and a circumferential interior wall 128 formed along the outer first surface 116 of the static cranial implant 114. The circumferential interior wall 128 extends upwardly from the base 130 to the exterior of the outer first surface 116 of the static cranial implant 114. The circumferential interior wall 128 extends upwardly from the base 130 to a point where it meets the outer first surface 116.

The circumferential recess 126 mentioned above is formed along the circumferential interior wall 128 of the cavity 122. As such, the annular circumferential recess 126 is defined by a lower wall 132, an upper wall 134, and a connecting wall 136 extending between the lower wall 132 and the upper wall 134. The connecting wall 136 of the annular circumferential recess 126 is separated from the circumferential interior wall 128 of the cavity 122 by the length of the upper and lower walls 134, 132.

Passage of the electrical leads 124 to exterior locations as desired is facilitated by the provision of radially extending slots 137 formed along the periphery of the static cranial implant 114. The slots 137 connect the interior of the annular circumferential recess 126 to the exterior of the static cranial implant 114 at the periphery of the static cranial implant 114. Passage of the electrical leads 124 to exterior locations is further facilitated by the provision of a guiding channel 138 formed in the outer first surface 116 of the static cranial implant 114 such that the guiding channel 138 is in alignment with the slots 137 formed in the periphery of the static cranial implant 114.

In particular, the outer first surface 116 includes a plurality of radially extending flanges 140 that extend outwardly of the peripheral wall of the static cranial implant 114. As such, each of the flanges 140 includes an upper surface 142 that defines the exterior of the outer first surface 16 of the static cranial implant 14 and a lower surface 144 that ultimately is positioned upon the cranium when the circular base 130 and a circumferential interior wall 128 are positioned in the resected portion of the cranium created during the installation process.

A cover member 146 is further provided for housing the functional neurosurgical implant 112. The cover member 146 is shaped and dimensioned for positioning within the cavity 122 and for rotation of both the cover member 146 and the functional neurosurgical implant 12 in a controlled manner.

The cover member 146 is generally disk shaped and includes an upper surface 148, a lower surface 150, and a perimeter sidewall 152 extending between the upper surface 148 and the lower surface 150 along edge 154 of the cover member 146. The upper surface 148 is generally smooth, but includes a textured portion 156 for gripping when it is desired to rotate the cover member 146 and the functional neurosurgical implant 112. The lower surface 150 includes a recess 158 shaped and dimensioned for housing the functional neurosurgical implant 112. The lower surface 150 also includes a base surface 160 surrounding the recess 158. The base surface 160 is shaped and dimensioned to sit upon the base 130 of the cavity 122.

Secure attachment of the cover member 146 within the cavity of the static cranial implant 114 is facilitated by the provision of a downwardly extending flange member 162 along the lower surface 150 of the cover member 146. The downwardly extending flange member 162 is shaped and dimensioned to engage the cavity 122.

As with the embodiment disclosed above with reference to FIGS. 1 to 8, the functional neurosurgical implant 112 of the present invention is selected from a variety of FDA-approved and experimental options for electrical, optical, mechanical, medicinal, and other treatment/monitoring devices designed for long term invasive treatment and/or disease-monitoring of patients requiring such attention.

In practice, the functional neurosurgical implant 112 is inserted into the cavity of the cover member 146. The low-profile cranial device 110 is then installed in a resected portion of the cranium using conventional installation techniques. In one embodiment, a craniotomy is performed with a diameter equal to the diameter of the static cranial implant 114 as defined by the circumferential interior wall 128. The static cranial implant 114, in particular, the circumferential interior wall 128, sits within the craniotomy, thus reducing the overall profile of the functional neurosurgical implant 112 to be held within the static cranial implant 114. The flanges 140 defining the outer first surface 116 of the static cranial implant 114 lie on top of the cranium and allow fixation of the low-profile cranial device 110 using screws, plates, bioadhesives, or other traditional or novel methods. The channel 138 formed within the flange allows the electrical leads 124 to access annular circumferential recess 126 for electrical lead spooling.

Figure 16:
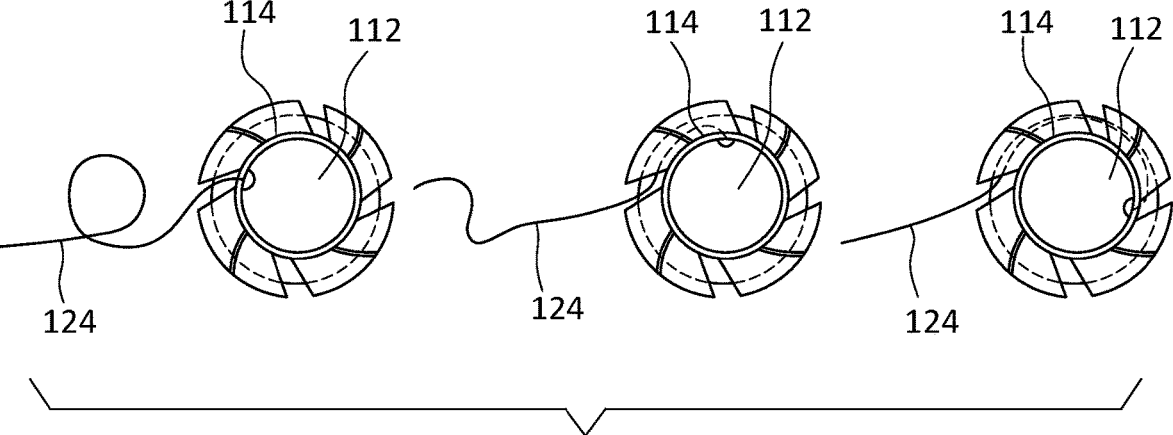
FIG. 16 is a schematic showing the sequence of steps in the operation of the cranial device shown in FIG. 9.
Figure 17:
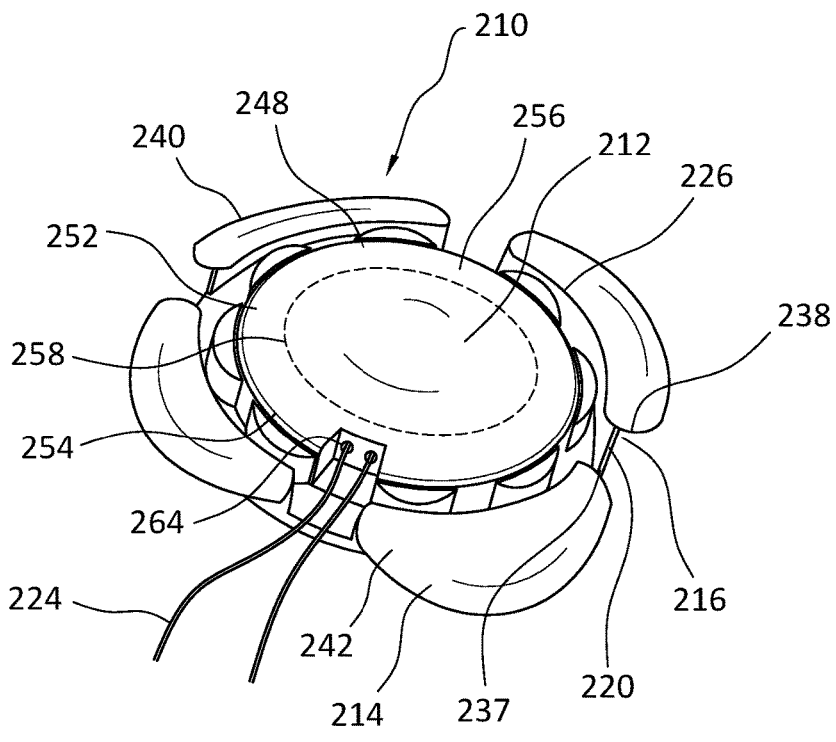
FIG. 17 is a perspective view of a third embodiment of a cranial device with a wire management structure.
Figure 18:
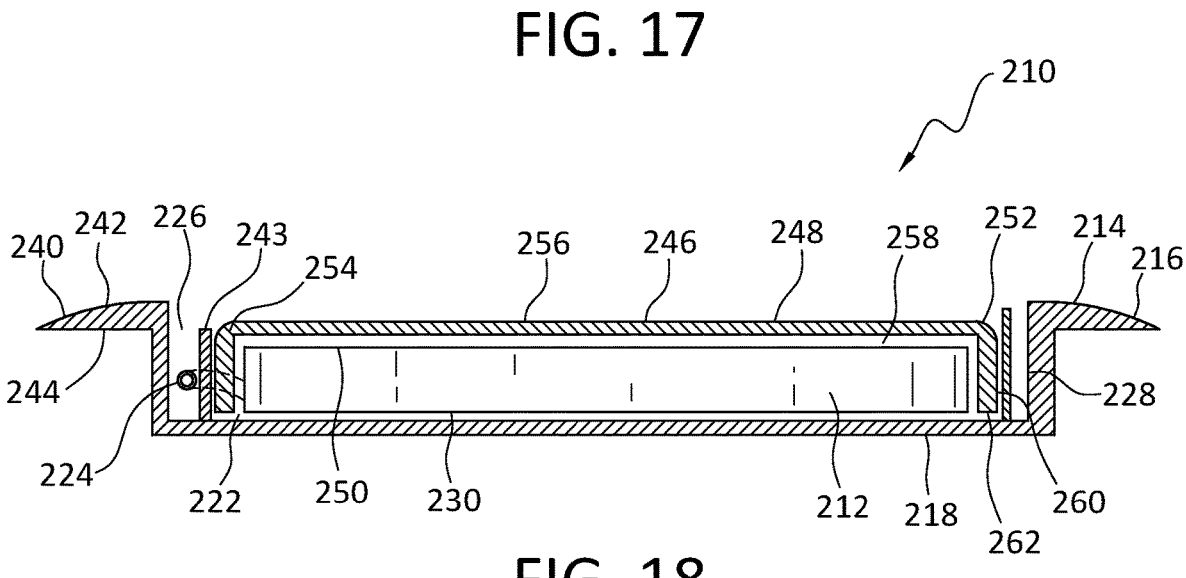
FIG. 18 is a cross sectional view of the cranial device shown in FIG. 17.
Figure 19:
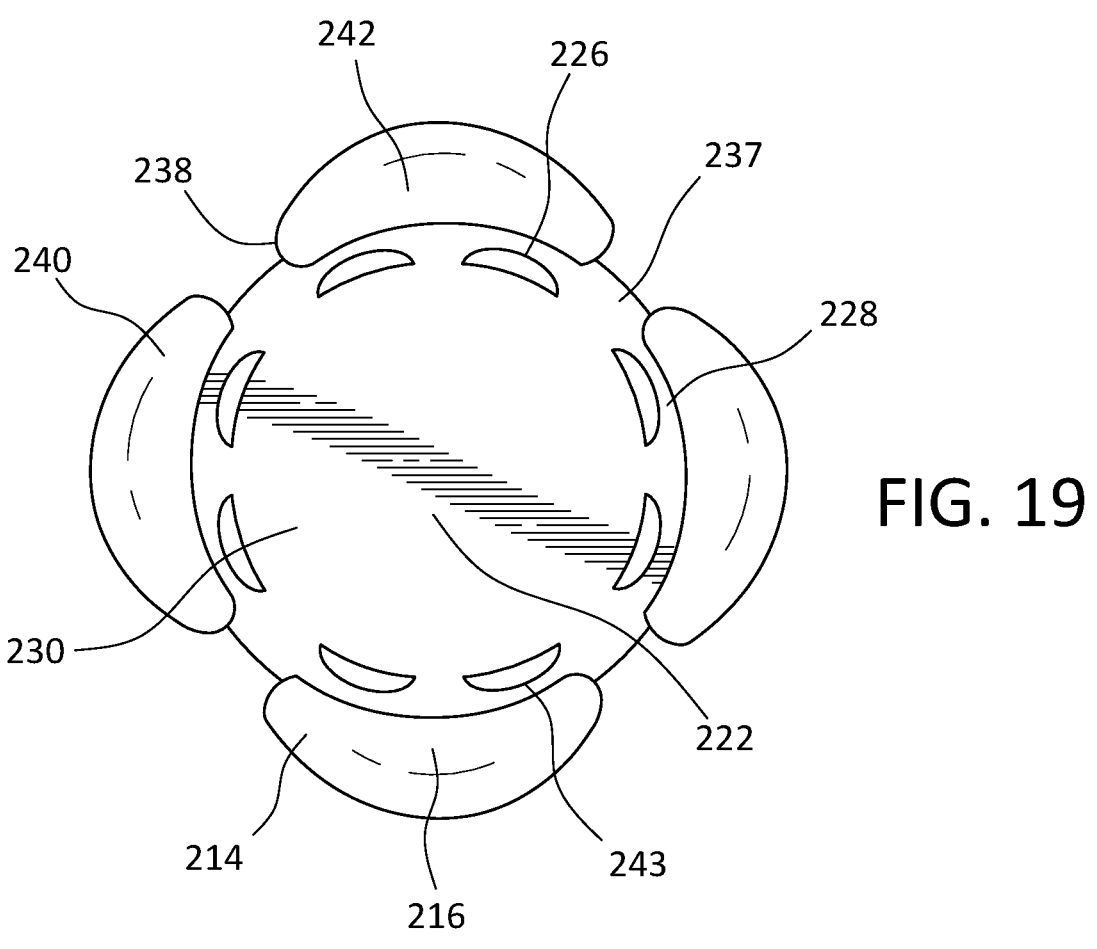
FIG. 19 is a top plan view of the cranial implant of the cranial device shown in FIG. 17.
Figure 20:
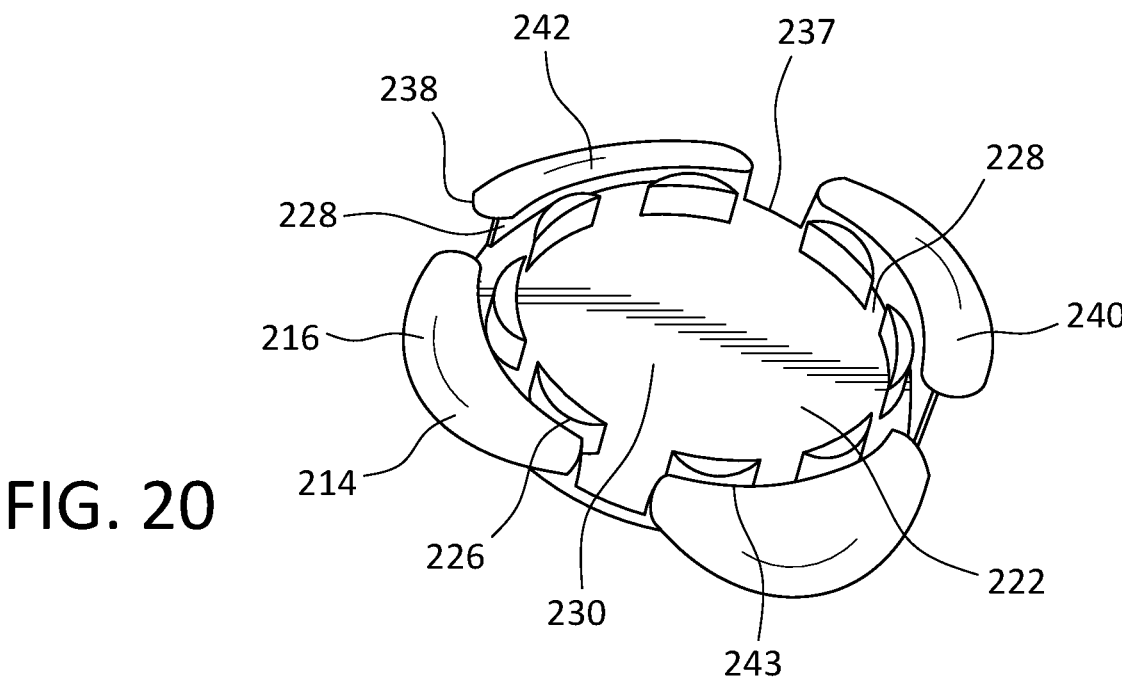
FIG. 20 is a perspective view of the cranial implant of the cranial device shown in FIG. 17.
Figure 21:
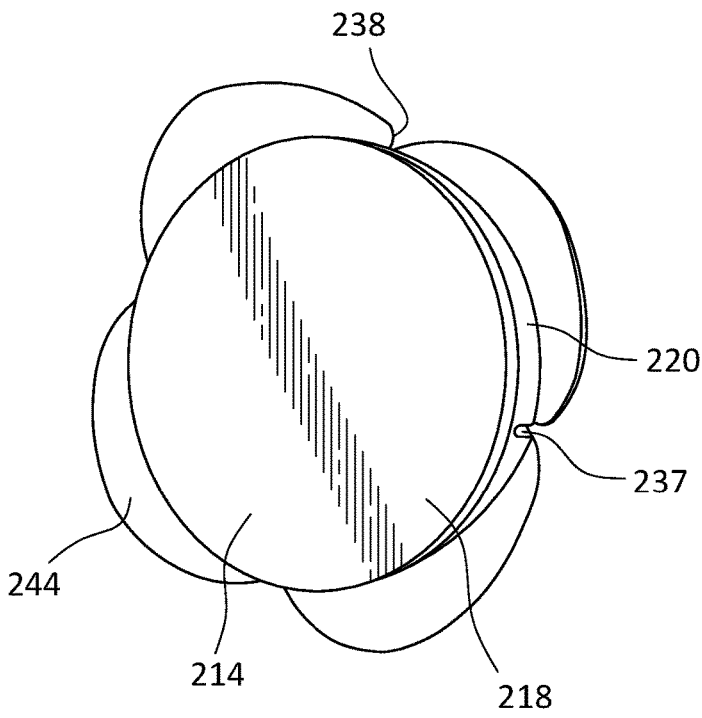
FIG. 21 is a bottom perspective view of the cranial implant of the cranial device shown in FIG. 17.

With low-profile cranial device 110 installed in a resected portion of the cranium, the electrical leads 124 of the functional neurosurgical implant 112 are connected thereto. The cover member 146 and the functional neurosurgical implant 112 are rotated (for example, in a clockwise direction as shown in FIG. 16) causing excess electrical lead length to spool into the annular circumferential recess 126 formed along the circumferential interior wall 128 of the cavity 122 formed within the static cranial implant 114. The user can continue to rotate the cover member 146 and the functional neurosurgical implant 112 until the desired amount of excess electrical lead length is spooled within the channel.

It is appreciated that the geometry of the low-profile cranial device 110 is such that there are no features between the outer surface of the rotating portion of the cover member 146/functional neurosurgical implant 112 and the annular circumferential recess 126 where the electrical leads 124 are spooled or stored. This is to allow the free rotation of the functional neurosurgical implant 112 and simultaneously allow the electrical leads 124 to fill the channel.

Referring to FIGS. 17 to 22, another embodiment of a low-profile cranial device 210 is disclosed. This embodiment employs a different internal structure for the cavity of the static cranial implant 214 that stores the electrical leads within the cavity. It also requires rotation and may be used with either a functional neurosurgical implant as disclosed above with reference to FIGS. 1 to 8, or a functional neurosurgical implant/cover member combination as disclosed above with reference to FIGS. 9 to 16. For the purposes of describing this embodiment, it will be described as used in conjunction with the functional neurosurgical implant/cover member combination.

The low-profile cranial device 210 is generally composed of a static cranial implant 214 and a functional neurosurgical implant 212. As will be appreciated based upon the following disclosure, the static cranial implant 214 is shaped and dimensioned to house the functional neurosurgical implant 212, with both being implanted within the cranium of a patient.

The static cranial implant 214 includes an outer (commonly convex) first surface 216 along the exterior side of the static cranial implant 214, an inner (commonly concave) second surface 218 along the interior side of the static cranial implant 214, and a peripheral wall 20 extending between the outer first surface 216 and the inner second surface 218. The static cranial implant 214 is shaped and dimensioned for engagement with the skull of the patient upon implantation in a manner well known to those skilled in the field of neurosurgical procedures.

The outer first surface 216 and inner second surface 218 of the static cranial implant 214 are preferably curved in a superior to inferior direction, a posterior to anterior direction, and a medial to lateral direction. The outer first surface 216 is substantially annular as the static cranial implant 214 includes a cavity 222 formed therein. The inner second surface 218 is a substantially continuous surface and ultimately defines the bottom wall of the static cranial implant 214.

The static cranial implant 214 has a preselected thickness, that is, the distance between the outer first surface 216 and the inner second surface 218, approximating the thickness of the cranium and not exceeding the space between the inner surface of the scalp and the outer surface of the dura, for example, in the range of around 1 millimeter to 25 millimeters (with areas of strategic bulking and/or thinning) and depending upon the strength of the materials used in the construction of the static cranial implant 214. Preferably, the static cranial implant 214 has a thickness of 1 millimeter to 12 millimeters. The static cranial implant 214 also includes a cavity 222 formed along the outer first surface 216. As with the prior embodiments, the cranial implant 214 is fabricated from a wide array of commonly available biomaterials as discussed above.

The static cranial implant 214 is constructed to hold the functional neurosurgical implant 212 in a manner allowing the electrical leads 224 to be wound up to store excess electrical lead length. This is achieved by forming an annular circumferential recess 226 within the cavity 222 and along the circular base 230 thereof.

In particular, the cavity 222 of the static cranial implant 214 is circular and is formed along the outer first surface 216 of the static cranial implant 214. The cavity 222 is defined by a circular base 230 and a circumferential interior wall 228 formed along the outer first surface 216 of the static cranial implant 214. The circumferential interior wall 228 extends upwardly from the base 230 to the exterior of the outer first surface 216 of the static cranial implant 214. The circumferential interior wall 228 extends upwardly from the base 230 to a point where it meets the outer first surface 216. Formed internally of the circumferential interior wall 228 is an annular upstanding wall 243. The annular upstanding wall 243 extends upwardly from the base 230 to a height slightly lower than that of the circumferential interior wall 228. As the annular upstanding wall 243 is positioned within the circumferential interior wall 228, the circumferential interior wall defines a diameter that is larger than the diameter defined by the annular upstanding wall 243. While the disclosed annular upstanding wall 243 is formed with multiple segments, it is appreciated the annular upstanding wall 243 could be of a continuous construction. The space between the circumferential interior wall 228 and the annular upstanding wall 243 defines the previously mentioned annular circumferential recess 226 in which the electrical leads 224 are gathered.

Passage of the electrical leads 224 to exterior locations as desired is facilitated by the provision of radially extending slots 237 formed along the periphery of the static cranial implant 214. The slots 237 connect the interior of the annular circumferential recess 226 to the exterior of the static cranial implant 214 at the periphery of the static cranial implant 214. Passage of the electrical leads 224 to exterior locations is further facilitated by the provision of a guiding channel 238 formed in the outer first surface 216 of the static cranial implant 214 such that the guiding channel 238 is in alignment with the slots 237 formed in the periphery of the static cranial implant 214.

The outer first surface 216 includes a plurality of radially extending flanges 240 that extends outwardly of the peripheral wall of the static cranial implant 214. As such, each of the flanges 240 includes an upper surface 242 that defines the exterior of the outer first surface 216 of the static cranial implant 214 and a lower surface 244 that ultimately is positioned upon the cranium when the circular base 230 and a circumferential interior wall 228 are positioned in the resected portion of the cranium created during the installation process.

A cover member 246 is further provided for housing the functional neurosurgical implant 212. The cover member 246 is shaped and dimensioned for positioning within the cavity 222 and for rotation of both the cover member 246 and the functional neurosurgical implant 212 in a controlled manner.

The cover member 246 is generally disk shaped and includes an upper surface 248, a lower surface 250, and a perimeter sidewall 252 extending between the upper surface 248 and the lower surface 250 along an edge 254 of the cover member 246. The upper surface 248 is generally smooth, but includes a textured portion 256 for gripping when it is desired to rotate the cover member 246 and functional neurosurgical implant 212. The lower surface 250 includes a recess 258 shaped and dimensioned for housing the functional neurosurgical implant 212. The lower surface 250 also includes a base surface 260 surrounding the recess 258. The base surface 260 is shaped and dimensioned to sit upon the base 230 of the cavity 222.

Secure attachment of the cover member 246 within the cavity of the static cranial implant 214 is facilitated by the provision of a downwardly extending flange member 262 along the lower surface 250 of the cover member 246. The downwardly extending flange member 262 is shaped and dimensioned to engage the upper edge of the annular upstanding wall 243.

As discussed above with reference to the prior embodiments, the functional neurosurgical implant 212 of the present invention is selected from a variety of FDA-approved and experimental options for electrical, optical, mechanical, medicinal, and other treatment/monitoring devices designed for long term invasive treatment and/or disease-monitoring of patients requiring such attention.

In practice, the functional neurosurgical implant 212 is inserted into the cavity of the cover member 246. The low-profile cranial device 210 is then installed in a resected portion of the cranium using conventional installation techniques. In one embodiment, a craniotomy is performed with a diameter equal to the diameter of the static cranial implant 214 as defined by the circumferential interior wall 228. The static cranial implant 214, in particular, the circumferential interior wall 228, sits within the craniotomy, thus reducing the overall profile of the functional neurosurgical implant 212 to be held within the static cranial implant 214 of the invention. The flanges 240 defining the outer first surface 216 of the static cranial implant 214 lie on top of the cranium and allow fixation of the low-profile cranial device 210 using screws, plates, bioadhesives, or other traditional or novel methods. The channel 238 formed within the flange allows the electrical leads 224 to access the circumferential recess 226 for electrical lead spooling.

Figure 22:
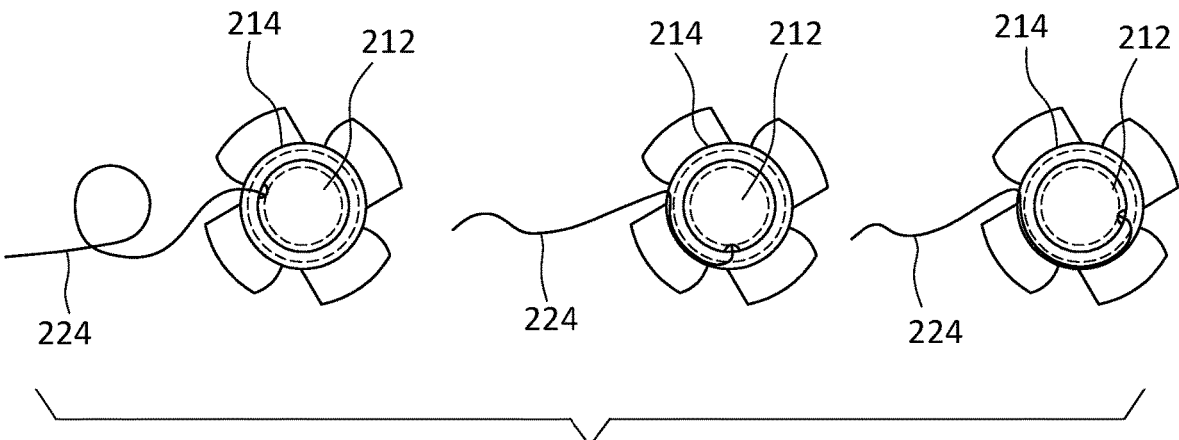
FIG. 22 is a schematic showing the sequence of steps in the operation of the cranial device shown in FIG. 17.
Figure 23:
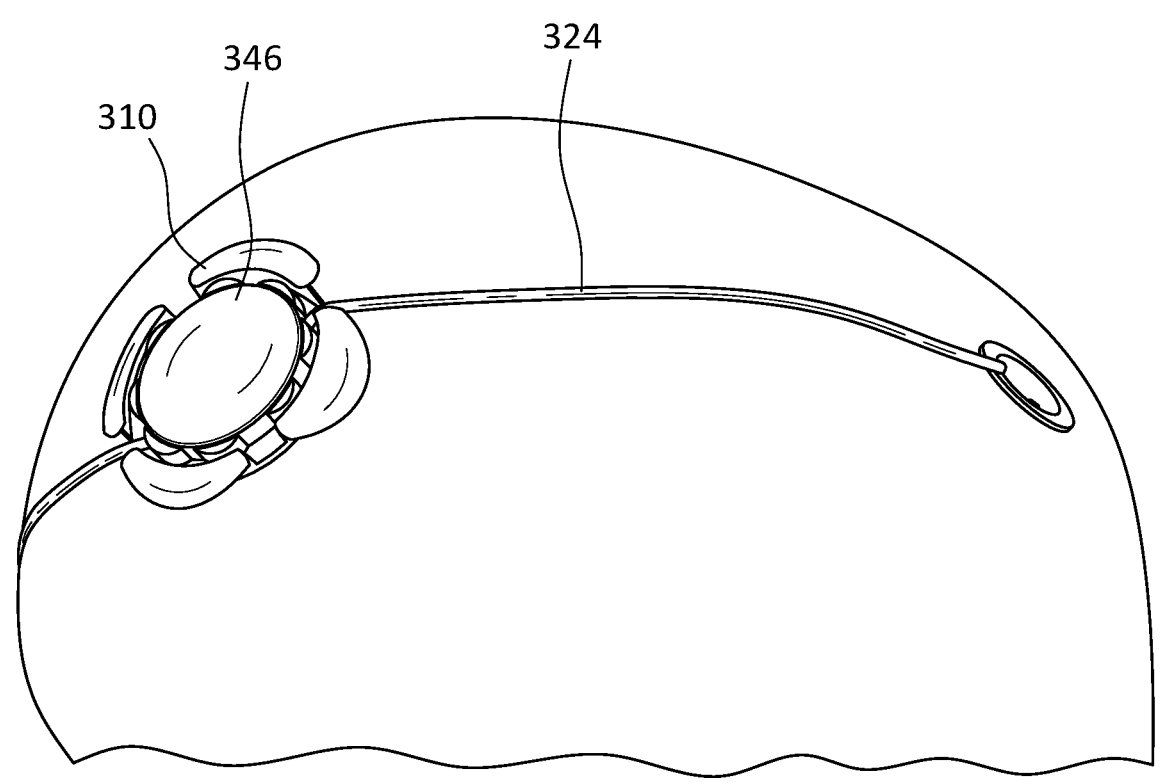
FIG. 23 is a perspective view of a fourth embodiment of a cranial device with a wire management structure in use.
Figure 24:
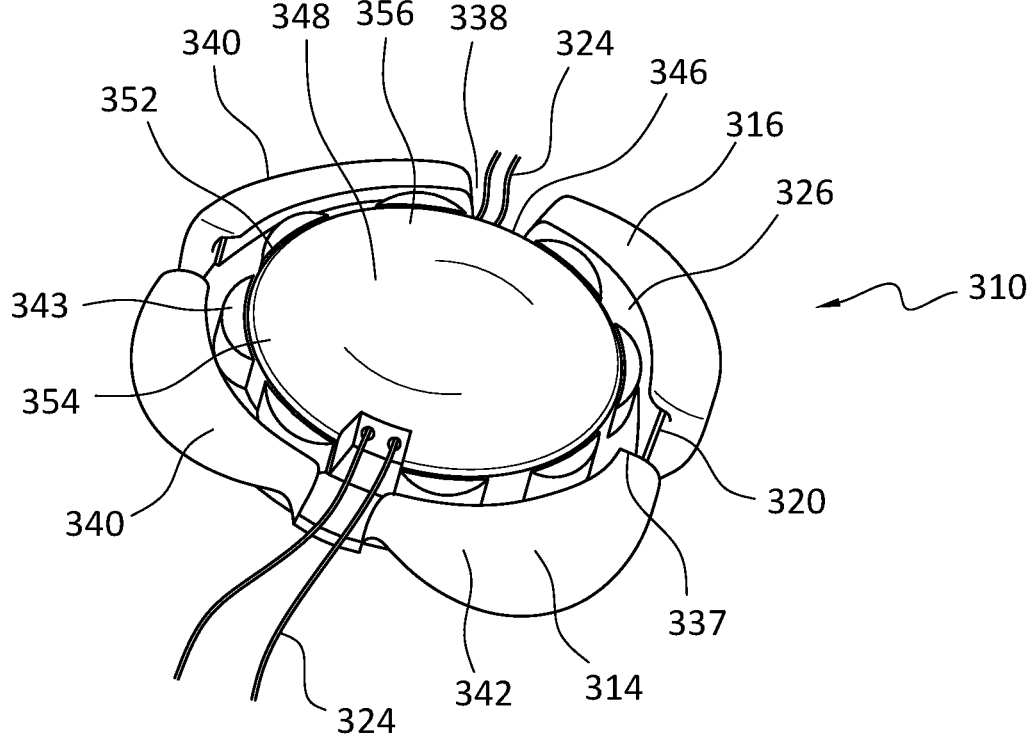
FIG. 24 is a perspective view of the cranial device shown in FIG. 23.
Figure 25:
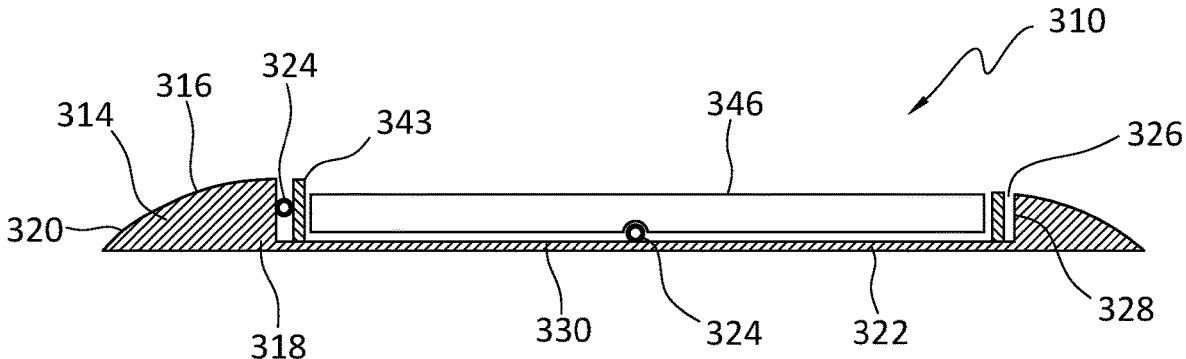
FIG. 25 is a cross sectional view of the cranial device shown in FIG. 23.
Figure 26:
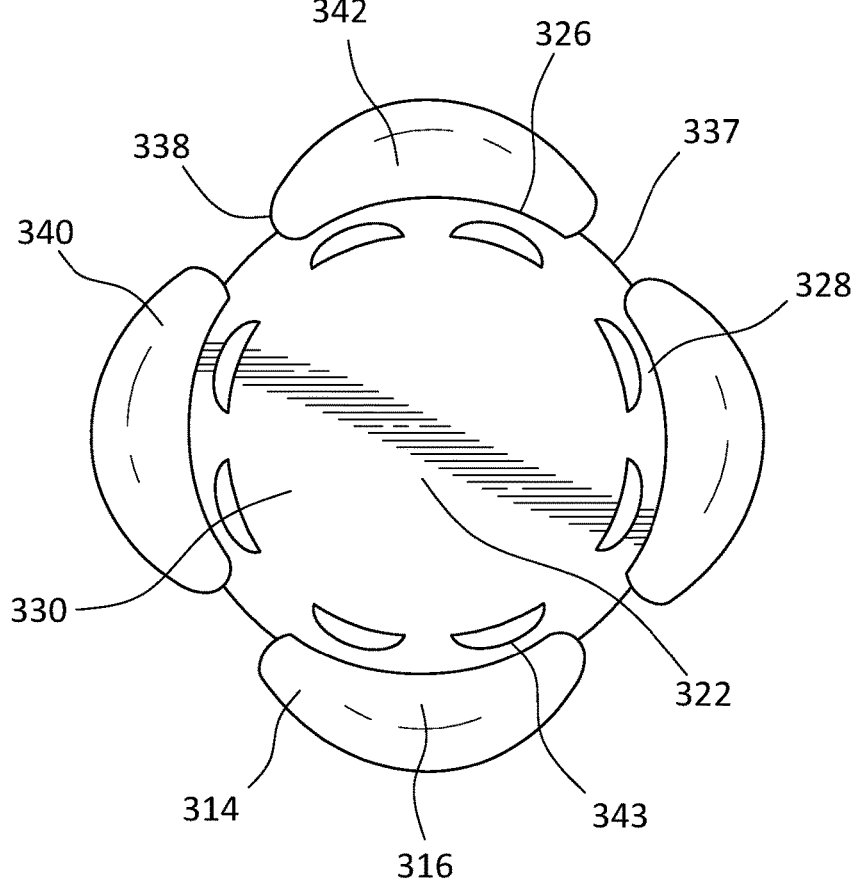
FIG. 26 is a top plan view of the cranial implant of the cranial device shown in FIG. 23.
Figure 27:
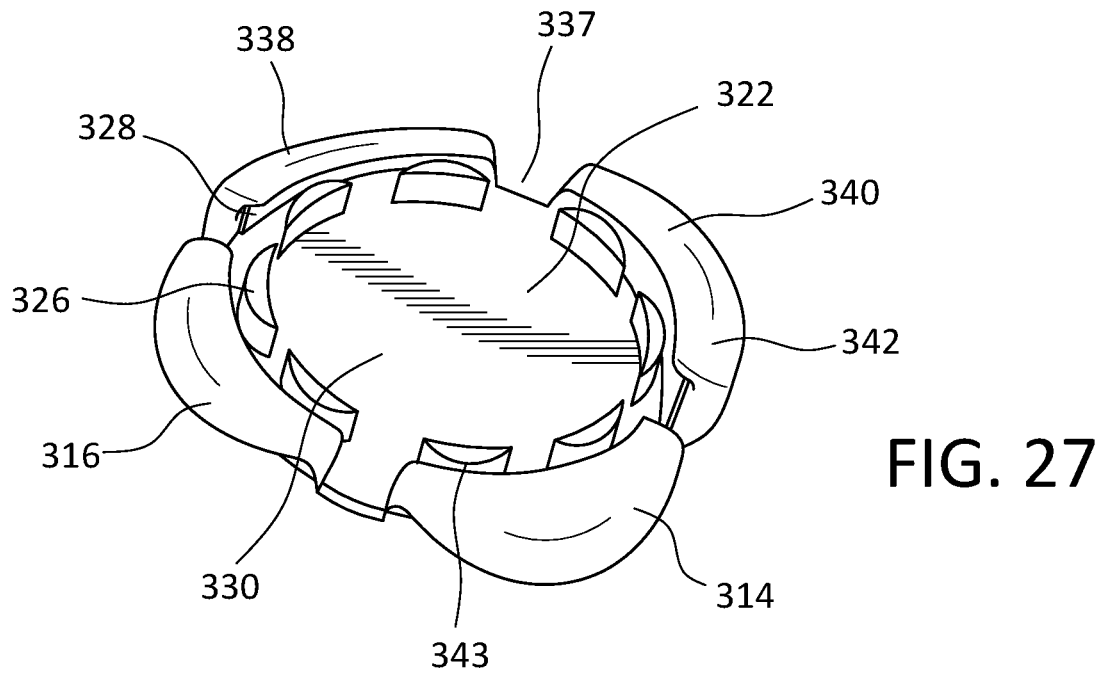
FIG. 27 is a perspective view of the cranial implant of the cranial device shown in FIG. 23.
Figure 28:
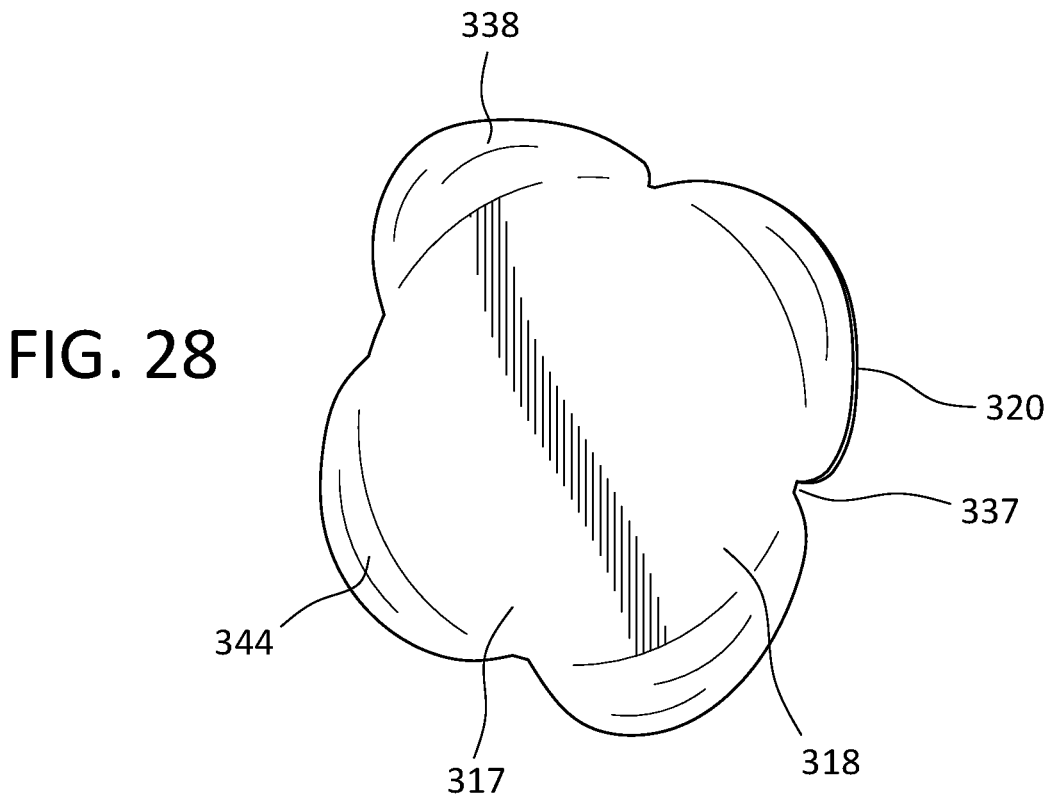
FIG. 28 is a bottom perspective view of the cranial implant of the cranial device shown in FIG. 23.

With low-profile cranial device 210 installed in a resected portion of the cranium, the electrical leads 224 of the functional neurosurgical implant 212 are passed into electrical connection members 264 within the cover member 246 for electrical connection with the functional neurosurgical implant 212 held within the cover member 246. The cover member 246 and the functional neurosurgical implant 212 are rotated (for example, in a counter-clockwise direction as shown in FIG. 22) causing excess electrical lead length to spool into the annular circumferential recess 226 formed along the circumferential interior wall 228 of the cavity 222 formed within the static cranial implant 214. While rotating, the electrical leads 224 are lifted adjacent the electrical connection members 264 so they pass over the annular upstanding wall 243. The user can continue to rotate the cover member 246 and the functional neurosurgical implant 212 until the desired amount of excess electrical lead length is spooled within the channel.

Referring to FIGS. 23 to 29, another embodiment of a low-profile cranial device 310 is disclosed. This embodiment employs wire management techniques as discussed above with regard to the prior embodiments but does not require the inclusion of a functional neurosurgical implant and is not designed for positioning within the intercranial space. It is designed for placement between a cranial access point (for example, a burr hole) and a functional neurological implant located at a remote position along the body (for example, adjacent the clavicle).

As with the prior embodiment, it requires rotation and may use the wire management structure disclosed with either the embodiment disclosed in FIGS. 1 to 8, or the embodiment disclosed with reference to FIGS. 17 to 22. For the purposes of describing this embodiment, it will be described as used in conjunction with the wire management structure disclosed in FIGS. 17 and 22.

The low-profile cranial device 310 is generally composed of a static cranial implant 314 and a central rotation member 346. The static cranial implant 314 includes an outer (commonly convex) first surface 316 along the exterior side of the static cranial implant 314, an inner (commonly concave) second surface 318 along the interior side of the static cranial implant 314, and a peripheral wall 320 extending between the outer first surface 316 and the inner second surface 318. The static cranial implant 314 is shaped and dimensioned for engagement with the skull of the patient upon implantation in a manner well known to those skilled in the field of neurosurgical procedures.

The outer first surface 316 and inner second surface 318 of the static cranial implant 314 are preferably curved in a superior to inferior direction, a posterior to anterior direction, and a medial to lateral direction. As will be appreciated based upon the following disclosure, the outer first surface 316 is substantially annular as the static cranial implant 314 includes a cavity 322 formed therein. The inner second surface 318 is a substantially continuous surface and ultimately defines the bottom wall of the static cranial implant 314.

In accordance with a preferred embodiment, the static cranial implant 314 has a preselected thickness, that is, the distance between the outer first surface 316 and the inner second surface 318, as thin as possible so that it is both functionally and aesthetically inobtrusive with respect to the anatomy where it is positioned (with areas of strategic bulking and/or thinning) and depending upon the strength of the materials used in the construction of the static cranial implant 314.

The static cranial implant 314 also includes a cavity 322 formed along the outer first surface 316.

As with the prior embodiments, the customized cranial implant 314 is fabricated from a wide array of commonly available biomaterials as discussed above.

As discussed above, the low-profile cranial device 310 provides a mechanism for allowing electrical leads 324 extending between a cranial access point and a functional neurological implant to be wound up to store excess electrical lead length. This is achieved by forming a circumferential recess 326 along the circumferential interior wall 328 of the cavity 322 in which the electrical lead is to be stored.

In particular, the cavity 322 of the static cranial implant 314 is circular and is formed along the outer first surface 316 of the static cranial implant 314. The cavity 322 is defined by a circular base 330 and a circumferential interior wall 328 formed along the outer first surface 316 of the static cranial implant 314. The circumferential interior wall 328 extends upwardly from the base 330 to the exterior of the outer first surface 316 of the static cranial implant 314. The circumferential interior wall 328 extends upwardly from the base 330 to a point where it meets the outer first surface 316. While a circular configuration for the cavity is disclosed herein it is appreciated the cavity may take a variety of shapes without departing from the spirit of the present invention.

Formed internally of the circumferential interior wall 328 is an annular upstanding wall 343. The annular upstanding wall 343 extends upwardly from the base 330 to a height slightly lower than that of the circumferential interior wall 328. As the annular upstanding wall 343 is positioned within the circumferential interior wall 328, the circumferential interior wall defines a diameter that is larger than the diameter defined by the annular upstanding wall 343. While the disclosed annular upstanding wall 343 is formed with multiple segments, it is appreciated the annular upstanding wall 343 could be of a continuous construction. The space between the circumferential interior wall 328 and the annular upstanding wall 343 defines the previously mentioned annular circumferential recess 326 in which the electrical leads 324 are gathered.

Passage of the electrical leads 324 to exterior locations as desired is facilitated by the provision of radially extending slots 337 formed along the periphery of the static cranial implant 314. The slots 337 connect the interior of the circumferential recess 326 to the exterior of the static cranial implant 314 at the periphery of the static cranial implant 314. Passage of the electrical leads 324 to exterior locations is further facilitated by the provision of a guiding channel 338 formed in the outer first surface 316 of the static cranial implant 314 such that the guiding channel 338 is in alignment with the slots 337 formed in the periphery of the static cranial implant 314.

In particular, the outer first surface 316 includes a plurality of radially extending flanges 340 that extend outwardly of the peripheral wall of the static cranial implant 314. As such, each of the flanges 340 includes an upper surface 342 that defines the exterior of the outer first surface 316 of the static cranial implant 314 and a lower surface 344 that is coextensive with the inner second surface 318 and ultimately is positioned upon the cranium.

A central rotation member 346 is further provided for holding the electrical lead and controlling take-up of the electrical lead into the circumferential recess 326. The central rotation member 346 is shaped and dimensioned for positioning within the cavity 322 and for rotation of the central rotation member 346 in a controlled manner.

The central rotation member 346 is generally disk shaped and includes an upper surface 348, a lower surface 350, and a perimeter sidewall 352 extending between the upper surface 348 and the lower surface 350 along edge 354 of the central rotation member 346. The upper surface 348 is generally smooth, but includes a textured portion 356 for gripping when it is desired to rotate the central rotation member 346. The lower surface 350 includes a slot 358 shaped and dimensioned for the passage of the electrical lead therethrough as it extends between the cranial access point and the functional neurological implant. The lower surface 350 also includes a base surface 360 surrounding the slot 358. The base surface 360 is shaped and dimensioned to sit upon the base 330 of the cavity 322.

Secure attachment of the central rotation member 346 within the cavity of the static cranial implant 314 is facilitated by the provision of a downwardly extending flange member 362 along the lower surface 350 of the central rotation member 346. The downwardly extending flange member 362 is shaped and dimensioned to engage the upper edge of the cavity 322 where the upper surface meets the circumferential interior wall 328.

Figure 29:
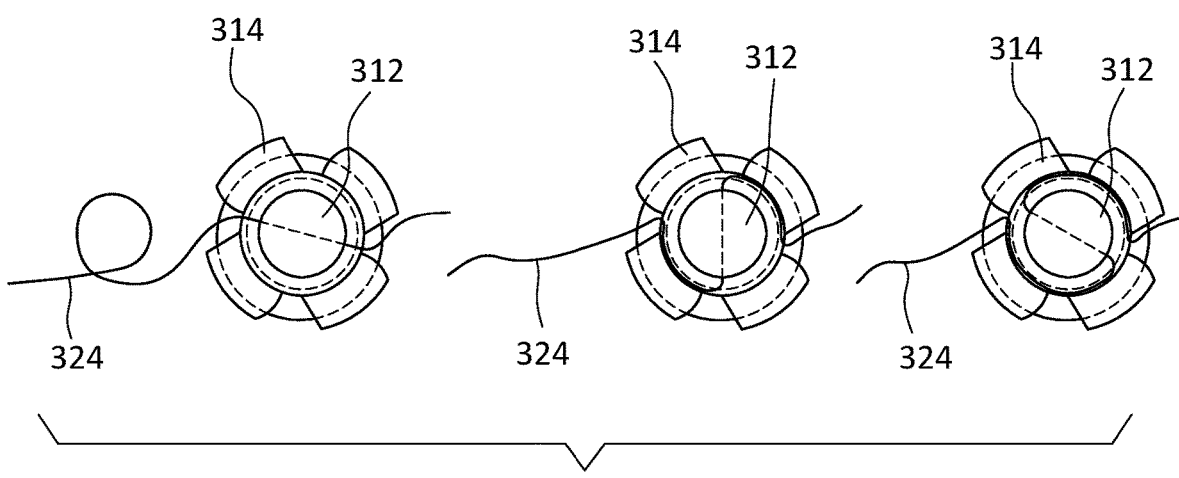
FIG. 29 is a schematic showing the sequence of steps in the operation of the cranial device shown in FIG. 23.
Figure 30:
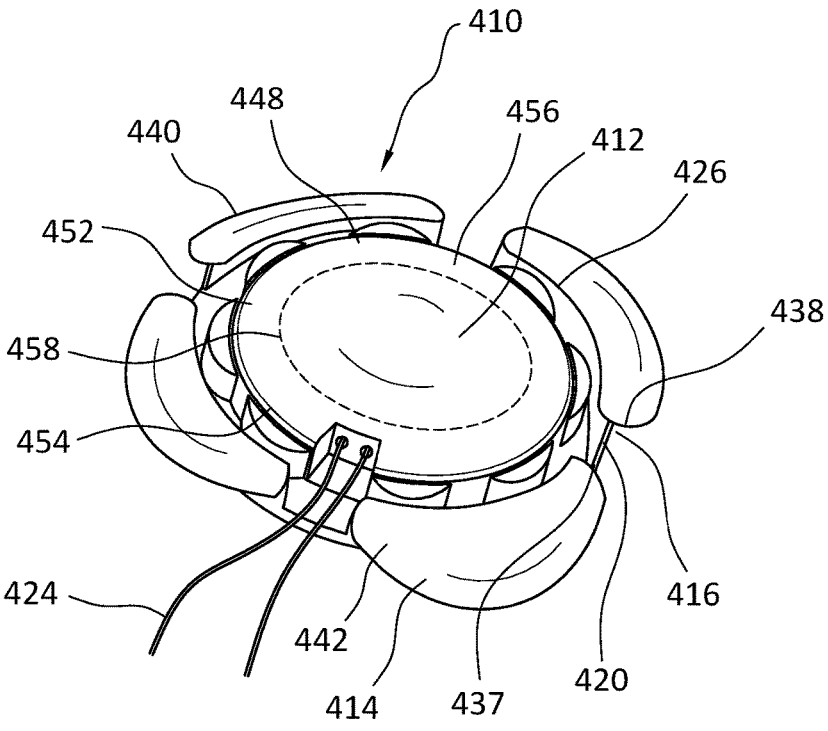
FIG. 30 is a perspective view of a fifth embodiment of a cranial device with a wire management structure.
Figure 31:
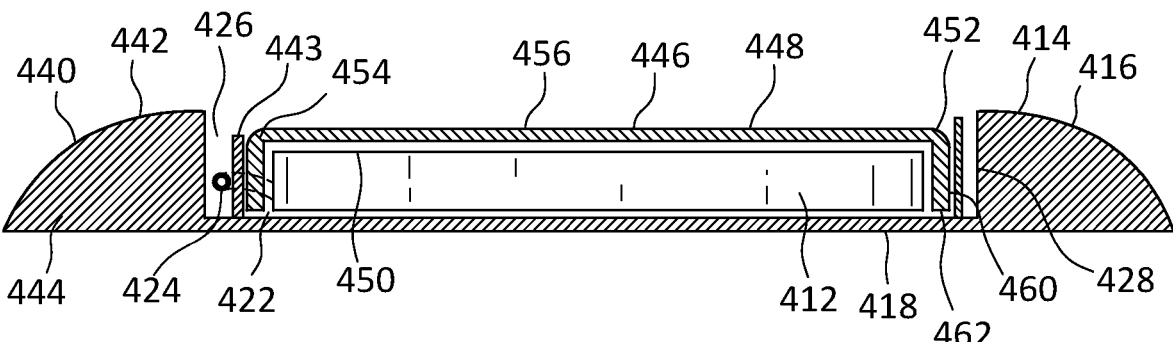
FIG. 31 is a cross sectional view of the cranial device shown in FIG. 30.
Figure 32:
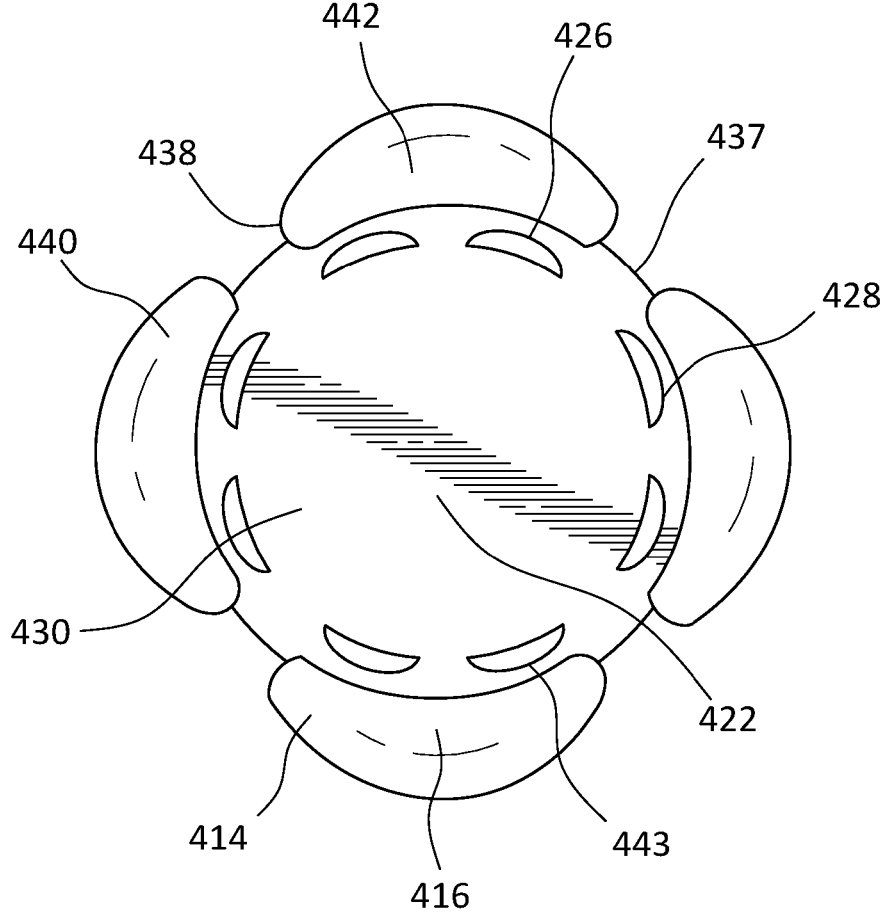
FIG. 32 is a top plan view of the cranial implant of the cranial device shown in FIG. 30.
Figure 33:
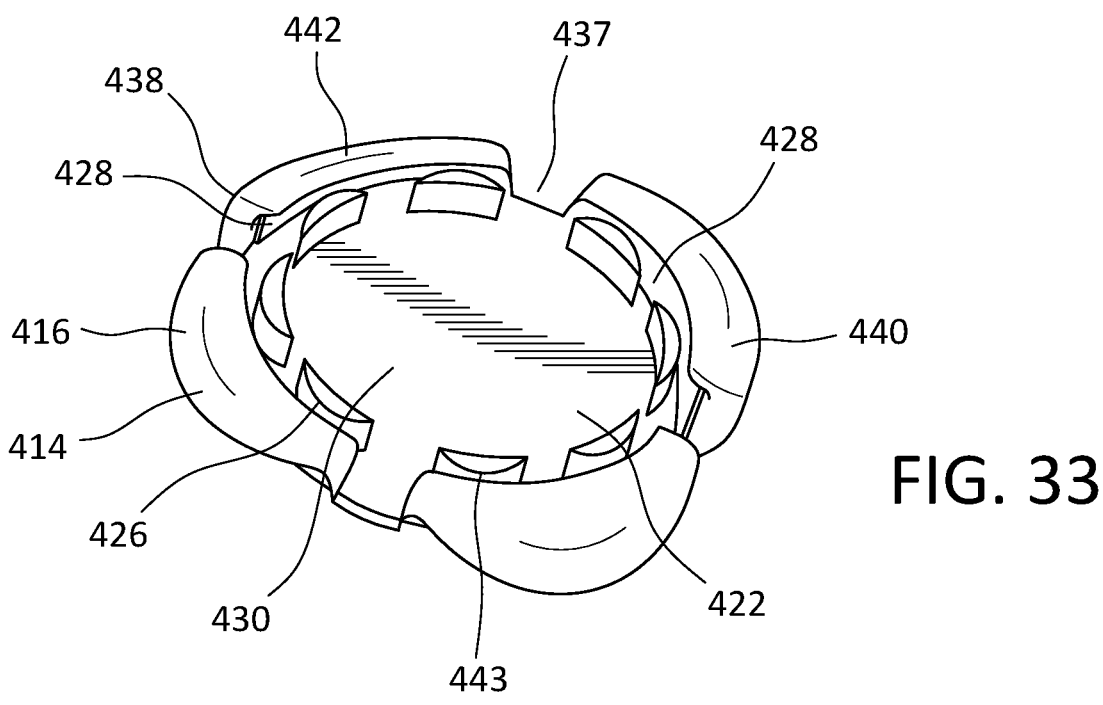
FIG. 33 is a perspective sectional view of the cranial implant of the cranial device shown in FIG. 30.
Figure 34:
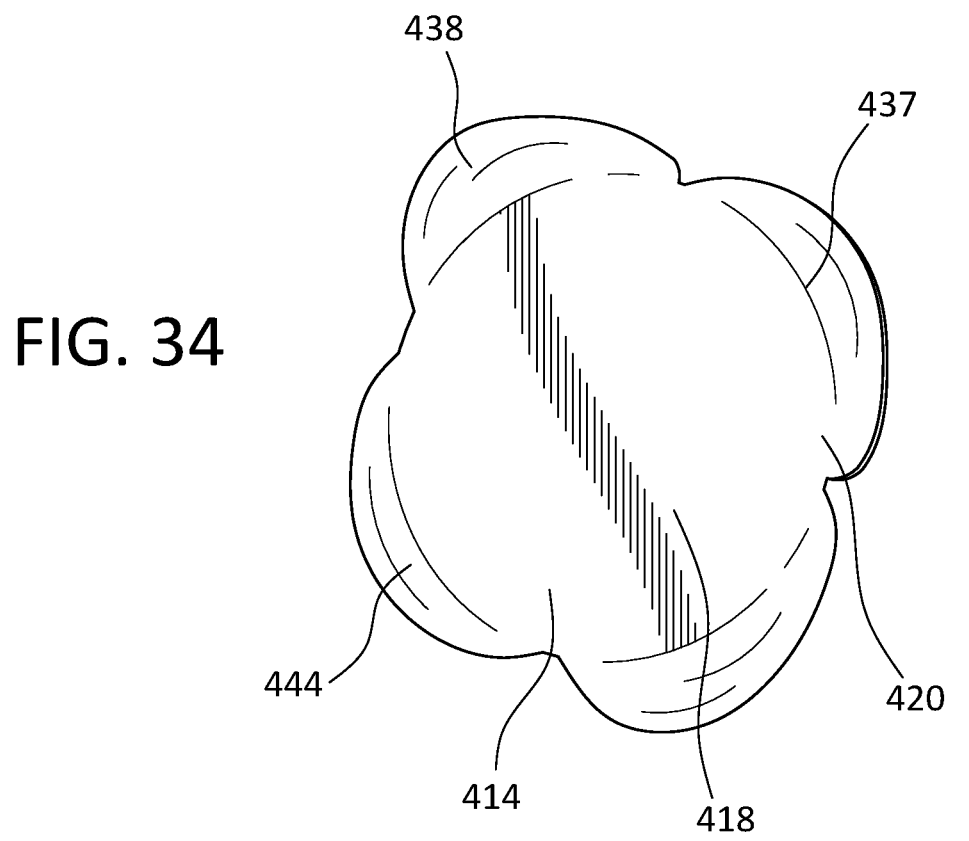
FIG. 34 is a bottom perspective view of the cranial implant of the cranial device shown in FIG. 30.
Figure 35:
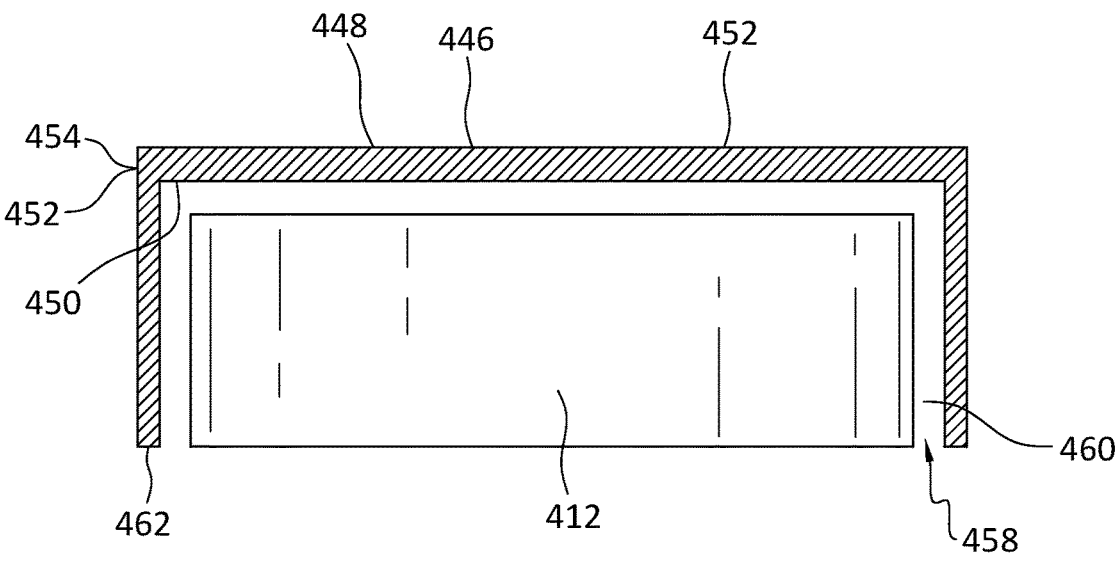
FIG. 35 is a cross sectional view showing the cover member housing the functional neurosurgical implant of the cranial device shown in FIG. 30.

In practice, the low-profile cranial device 310 is installed at a desired location, preferably, after the electrical lead is run between the cranial access point and the functional neurological implant. With low-profile cranial device 310 installed, the electrical lead 324 is passed through the slot 358 of the central rotation member 346 and the central rotation member 346 is positioned within the cavity 322. The central rotation member 346 is rotated (for example, in a counter-clockwise direction as shown in FIG. 29) causing excess electrical lead length to spool into the circumferential recess 326 formed along the circumferential interior wall 328 of the cavity 322 formed within the static cranial implant 314. While rotating, the electrical leads 324 are lifted adjacent the central rotation member 346 so they pass over the annular upstanding wall 343. The user can continue to rotate the central rotation member 346 until the desired amount of excess electrical lead length is spooled within the channel.

Referring to FIGS. 30 to 36, another embodiment of a low-profile cranial device 410 is disclosed. This embodiment employs wire management techniques as discussed above with regard to the prior embodiments and provides for integration with a functional neurosurgical implant, but is not designed for positioning within the intercranial space. It is designed for placement at a remote point along the body, for example, adjacent the clavicle.

As with the prior embodiment, it requires rotation and may use the wire management structure disclosed with either the embodiment disclosed in FIGS. 1 to 8, or the embodiment disclosed with reference to FIGS. 17 to 22. For the purposes of describing this embodiment, it will be described as used in conjunction with the wire management structure disclosed in FIGS. 17 and 22. Also, it may use the functional neurosurgical implant as disclosed with reference to the embodiment of FIGS. 1 to 8 or the functional neurosurgical implant/cover member as disclosed with reference to the embodiment of FIGS. 9 to 16. For the purposes of describing this embodiment, it will be described as used in conjunction with the functional neurosurgical implant/ cover member wire management structure disclosed in FIGS. 9 to 16.

The low-profile cranial device 410 is generally composed of a static cranial implant 414 and a functional neurosurgical implant 412. As will be appreciated based upon the following disclosure, the static cranial implant 414 is shaped and dimensioned to house the functional neurosurgical implant 412, with both being implanted within the cranium of a patient.

The static cranial implant 414 includes an outer (commonly convex) first surface 416 along the exterior side of the static cranial implant 414, an inner (commonly concave) second surface 418 along the interior side of the static cranial implant 414, and a peripheral wall 420 extending between the outer first surface 416 and the inner second surface 418.

The outer first surface 416 and inner second surface 418 of the static cranial implant 414 are preferably curved in a superior to inferior direction, a posterior to anterior direction, and a medial to lateral direction. The outer first surface 416 is substantially annular as the static cranial implant 414 includes a cavity 422 formed therein. The inner second surface 418 is a substantially continuous surface and ultimately defines the bottom wall of the static cranial implant 414.

In accordance with a preferred embodiment, the static cranial implant 414 has a preselected thickness, that is, the distance between the outer first surface 416 and the inner second surface 418, which is as thin as possible so that it is both functionally and aesthetically inobtrusive with respect to the anatomy where it is positioned. It is further appreciated areas of strategic bulking and/or thinning may be employed depending upon the strength of the materials used in the construction of the static cranial implant 414. The static cranial implant 414 also includes a cavity 422 formed along the outer first surface 416.

As with the prior embodiments, the cranial implant 414 is fabricated from a wide array of commonly available biomaterials.

The static cranial implant 414 is constructed to hold the functional neurosurgical implant 412 in a manner allowing the electrical leads 424 to be wound up to store excess electrical lead length. This is achieved by forming an annular circumferential recess 426 within the cavity 422 and along the circular base 430 thereof.

In particular, the cavity 422 of the static cranial implant 414 is circular and is formed along the outer first surface 416 of the static cranial implant 414. The cavity 422 is defined by a circular base 430 and a circumferential interior wall 428 formed along the outer first surface 416 of the static cranial implant 414. The circumferential interior wall 428 extends upwardly from the base 430 to the exterior of the outer first surface 416 of the static cranial implant 414. The circumferential interior wall 428 extends upwardly from the base 430 to a point where it meets the outer first surface 416. Formed internally of the circumferential interior wall 428 is an annular upstanding wall 443. The annular upstanding wall 443 extends upwardly from the base 430 to a height slightly lower than that of the circumferential interior wall 428. As the annular upstanding wall 443 is positioned within the circumferential interior wall 428, the circumferential interior wall defines a diameter that is larger than the diameter defined by the annular upstanding wall 443. While the disclosed annular upstanding wall 443 is formed with multiple segments, it is appreciated the annular upstanding wall 443 could be of a continuous construction. The space between the circumferential interior wall 428 and the annular upstanding wall 443 defines the previously mentioned annular circumferential recess 426 in which the electrical leads are gathered.

Passage of the electrical leads 424 to exterior locations as desired is facilitated by the provision of radially extending slots 437 formed along the periphery of the static cranial implant 414. The slots 437 connect the interior of the static cranial implant 414 to the exterior of the static cranial implant 414 at the periphery of the static cranial implant 414. Passage of the electrical leads 424 to exterior locations is further facilitated by the provision of a guiding channel 438 formed in the outer first surface 416 of the static cranial implant 414 such that the guiding channel 438 is in alignment with the slots 437 formed in the periphery of the static cranial implant 414.

The outer first surface 416 includes a plurality of radially extending flanges 440 that extend outwardly of the peripheral wall of the static cranial implant 414. As such, each of the flanges 440 includes an upper surface 442 that defines the exterior of the outer first surface 16 of the static cranial implant 14 and a lower surface 444 coextensive with the inner second surface 418 and ultimately is positioned upon the cranium.

A cover member 446 is further provided for housing the functional neurosurgical implant 412. The cover member 446 is shaped and dimensioned for positioning within the cavity 422 and for rotation of both the cover member 446 and the functional neurosurgical implant 412 in a controlled manner.

The cover member 446 is generally disk shaped and includes an upper surface 448, a lower surface 450, and a perimeter sidewall 452 extending between the upper surface 448 and the lower surface 450 along edge 454 of the cover member 446. The upper surface 448 is generally smooth, but includes a textured portion 456 for gripping when it is desired to rotate the cover member 446 and functional neurosurgical implant 412. The lower surface 450 includes a recess 458 shaped and dimensioned for housing the functional neurosurgical implant 412. The lower surface 450 also includes a base surface 460 surrounding the recess 458. The base surface 460 is shaped and dimensioned to sit upon the base 430 of the cavity 422.

Secure attachment of the cover member 446 within the cavity of the static cranial implant 414 is facilitated by the provision of a downwardly extending flange member 462 along the lower surface 450 of the cover member 446. The downwardly extending flange member 462 is shaped and dimensioned to engage the cavity of the static cranial implant 414.

As discussed above with reference to the prior embodiments, the functional neurosurgical implant 412 of the present invention is selected from a variety of FDA-approved and experimental options for electrical, optical, mechanical, medicinal, and other treatment/monitoring devices designed for long term invasive treatment and/or disease-monitoring of patients requiring such attention.

In practice, the functional neurosurgical implant 412 is inserted into the cavity of the cover member 446. The low-profile cranial device 410 is then installed in a desired location.

Figure 36:
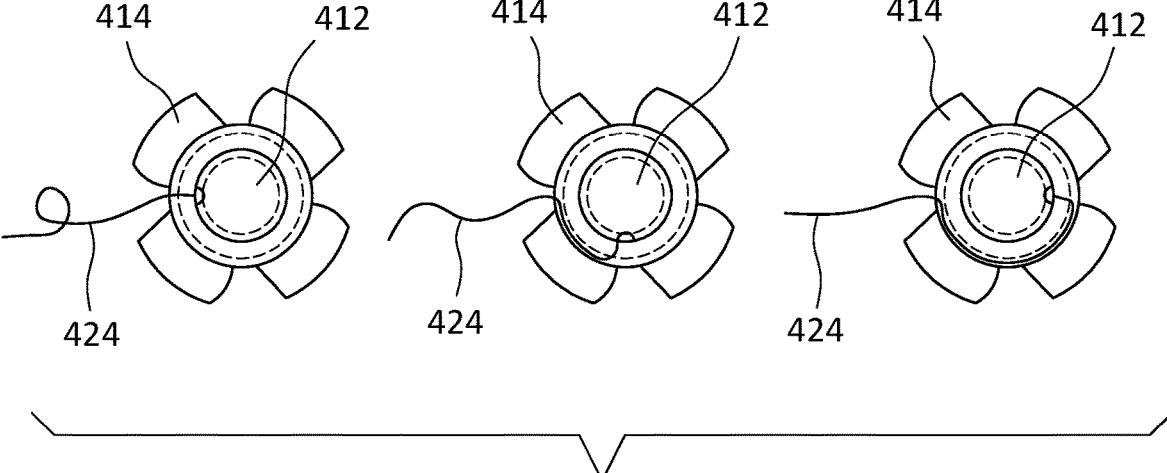
FIG. 36 is a schematic showing the sequence of steps in the operation of the cranial device shown in FIG. 30.

With the low-profile cranial device 410 installed, the electrical leads 424 of the functional neurosurgical implant 412 are passed into electrical connection members 464 within the cover member 446 for electrical connection with the functional neurosurgical implant 412 and held within the cover member 446. The cover member 446 and the functional neurosurgical implant 412 are rotated (for example, in a counter-clockwise direction as shown in FIG. 36) causing excess electrical lead length to spool into the annular circumferential recess 426 formed along the circumferential interior wall 428 of the cavity 422 formed within the static cranial implant 414. While rotating, the electrical leads 424 are lifted adjacent the electrical connection members 464 so they pass over the annular upstanding wall 443. The user can continue to rotate the cover member 446 and the functional neurosurgical implant 412 until the desired amount of excess electrical lead length is spooled within the channel.

Regardless of the embodiment discussed above, it is important that the device be locked in position once the electrical leads are properly wrapped into position as desired. This may be achieved in various ways.

Figures 37, 38, 39:
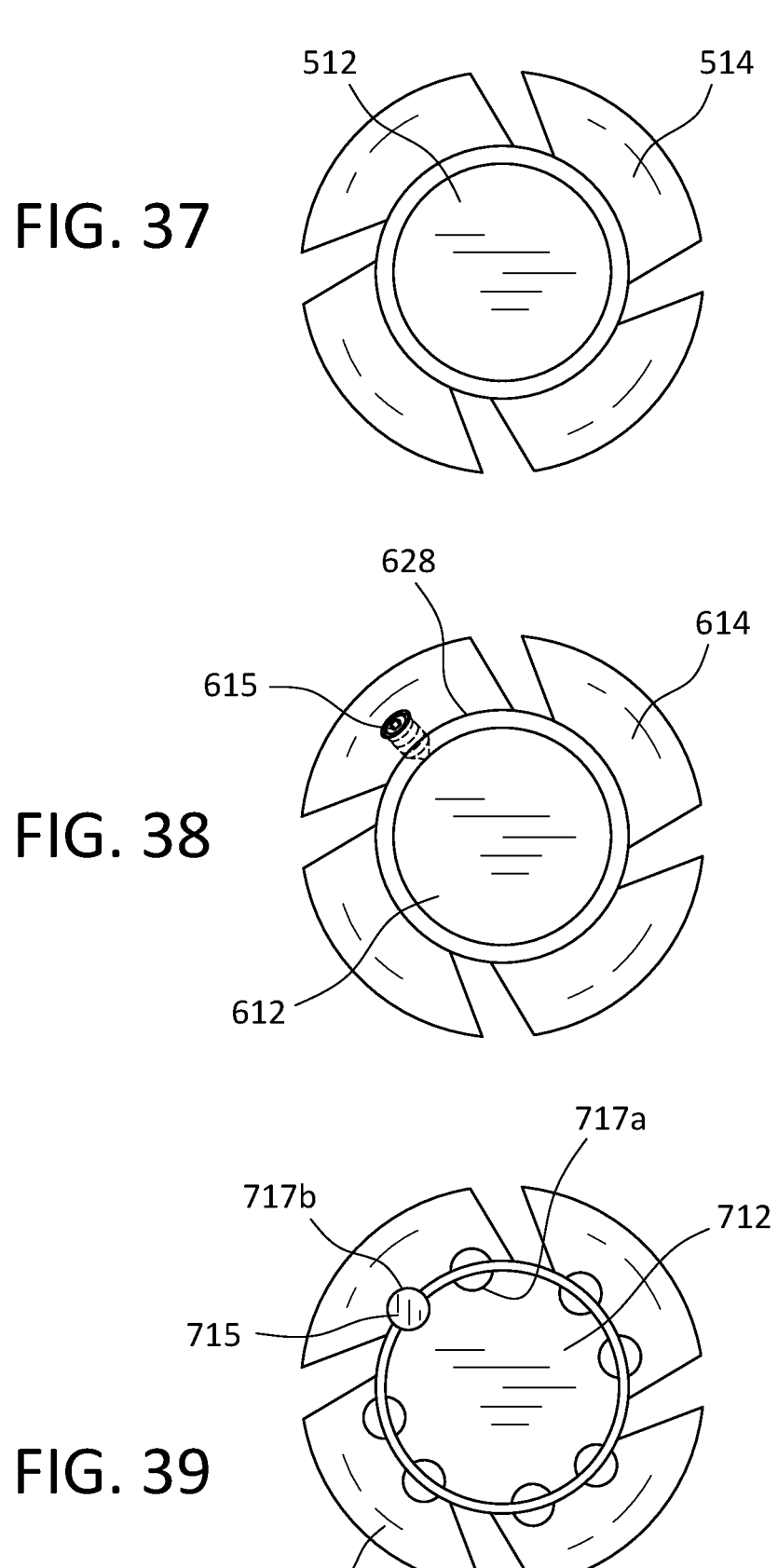
FIGS. 37 to 41 are top schematic views of various other embodiments.

For example, and with reference to FIG. 37, the functional neurosurgical implant 512 (or cover) is shaped and dimensioned such that sufficient friction exists between the functional neurosurgical implant 512 (or cover) and the static cranial implant 514 to hold the functional neurosurgical implant 512 (or cover) in position relative to the static cranial implant.

In accordance with another embodiment shown with reference to FIG. 38, the static cranial implant 614 is provided with a set screw 615 that acts upon the functional neurosurgical implant 612 (or cover) to hold it in position once the functional neurosurgical implant 612 (or cover) is rotated and the electrical leads are properly stored.

In particular, and in accordance with an embodiment, the set screw 615 is positioned within the circumferential interior wall 628 and extends therethrough such that the tip of the set screw 615 may be selectively brought into engagement with the functional neurosurgical implant 612 (or cover).

In accordance with another embodiment shown with reference to FIG. 39, a lug or post 715 is selectively inserted between the functional neurosurgical implant 712 (or cover) and the static cranial implant 714. For example, a series of grooves 717a, 717b may be formed in both the functional neurosurgical implant 712 (or cover) and the static cranial implant 714. Once the electrical lead is properly positioned, the medical practitioner may position the lug or post 715 within opposed and aligned grooves 717a, 717b of the functional neurosurgical implant 712 (or cover) and the static cranial implant 714. The lug or post 715 then functions to prevent subsequent relative movement of the functional neurosurgical implant 712 (or cover) and the static cranial implant 714.

Figures 40, 41:
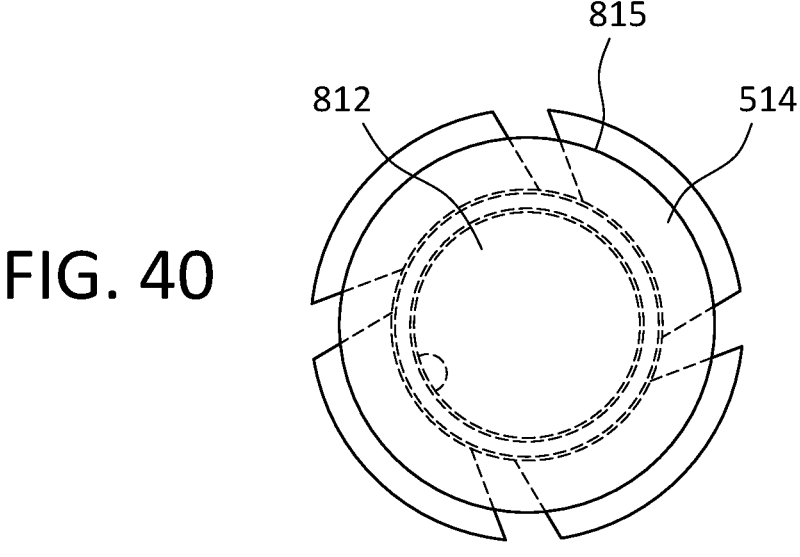

In accordance with another embodiment shown with reference to FIG. 40, an overlay 815 is provided for selective positioning over the functional neurosurgical implant 812 (or cover) and the static cranial implant 814 once the electrical lead has been drawn into the static cranial implant 814, For example, the overlay 815 is shaped and dimensioned to fit over both the functional neurosurgical implant 812 (or cover) and the static cranial implant 814. The overlay 815 includes downwardly extending members or simple frictionally engaging surfaces that interact with both the functional neurosurgical implant 812 (or cover) and the static cranial implant 814 to prevent subsequent relative movement of the functional neurosurgical implant 812 (or cover) and the static cranial implant 814.

In accordance with another embodiment shown with reference to FIG. 41, a ratchet mechanism (with or without a release mechanism) 915 is integrated between the functional neurosurgical implant 912 (or cover) and the static cranial implant 914. The ratchet mechanism 915 allows for rotation of the functional neurosurgical implant 912 (or cover) relative to the static cranial implant 914 in one direction causing the electrical leads to be drawn into the static cranial implant 914 and prevents subsequent rotation in the opposite direction.

The various embodiments disclosed above provide an easy and intuitive way to store excess lead length while also housing a device attached to the electrical leads. An efficient motion of rotating allows a quick solution to the problem of having to manage excess length. It also potentially protects the leads from damage due to external forces by covering the leads. The cranial device may have a range of sizes of channels or areas for storing excess lead lengths and diameters.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A low-profile cranial device adapted for covering and protecting electrical leads, comprising:
    a static cranial implant shaped and dimensioned for housing a functional neurosurgical implant including electrical leads, the static cranial implant includes an outer first surface along an exterior side of the static cranial implant, an inner second surface along an interior side of the static cranial implant, and a peripheral wall extending between the outer first surface and the inner second surface; and
    a cavity formed along the outer first surface of the static cranial implant, the cavity being shaped and dimensioned to house the functional neurosurgical implant in a manner allowing the electrical leads to be wound up to store excess electrical lead length;
    wherein the cavity is defined by a circular base and a circumferential interior wall formed along the outer first surface of the static cranial implant, and the circumferential interior wall extends upwardly from the base to the exterior of the outer first surface of the static cranial implant to a point where it meets the outer first surface, and an annular upstanding wall is formed internally of the circumferential interior wall, the annular upstanding wall extending upwardly from the base to a height slightly lower than that of the circumferential interior wall.

2. The low-profile cranial device according to claim 1, wherein the static cranial implant is shaped and dimensioned for positioning within an intercranial space.

3. The low-profile cranial device according to claim 1, wherein the static cranial implant is shaped and dimensioned for positioning between a skull and a scalp.

4. The low-profile cranial device according to claim 1, further including a functional neurosurgical implant.

5. The low-profile cranial device according to claim 4, wherein the functional neurosurgical implant is generally disk shaped and includes an upper surface, a lower surface, and a perimeter sidewall extending between the upper surface and the lower surface along an edge of the functional neurosurgical implant.

6. The low-profile cranial device according to claim 1, wherein the static cranial implant includes an annular circumferential recess along the circumferential interior wall of the cavity.

7. The low-profile cranial device according to claim 6, wherein the static cranial implant has a thickness between the outer first surface and the inner second surface of between 1 millimeter to 25 millimeters.

8. The low-profile cranial device according to claim 1, wherein the cranial implant is fabricated from PMMA (Poly(methyl methacrylate)), PEEK (Polyether ether ketone), PEKK (Polyetherketoneketone), porous polyethylene, titanium alloy, allograft, autograft, and xenograft.

9. The low-profile cranial device according to claim 8, wherein the static cranial implant allows for transmission of ultrasound waves.

10. The low-profile cranial device according to claim 1, wherein the cavity is circular and is formed along the outer first surface of the static cranial implant.

11. The low-profile cranial device according to claim 1, further including a cover member in which the functional neurosurgical implant is positioned.

12. The low-profile cranial device according to claim 1, wherein a cover member is further provided for housing the functional neurosurgical implant, and the cover member is shaped and dimensioned for positioning within the cavity and for rotation of both the cover member and the functional neurosurgical implant in a controlled manner.

13. A low-profile cranial device adapted for covering and protecting electrical leads, comprising:

a static cranial implant shaped and dimensioned for housing a functional neurosurgical implant, the static cranial implant includes an outer first surface along an exterior side of the static cranial implant, an inner second surface along an interior side of the static cranial implant, and a peripheral wall extending between the outer first surface and the inner second surface;

a cavity formed along the outer first surface of the static cranial implant; and a central rotation member shaped and dimensioned for positioning within the cavity and for rotation of the central rotation member;

wherein the cavity is defined by a circular base and a circumferential interior wall formed along the outer first surface of the static cranial implant, and the circumferential interior wall extends upwardly from the base to an exterior of the outer first surface of the static cranial implant to a point where it meets the outer first surface, and an annular upstanding wall is formed internally of the circumferential interior wall, the annular upstanding wall extending upwardly from the base to a height slightly lower than that of the circumferential interior wall.

14. The low-profile cranial device according to claim 13, wherein the static cranial implant is shaped and dimensioned for positioning between a skull and a scalp.

15. The low-profile cranial device according to claim 13, wherein the annular upstanding wall is positioned within the circumferential interior wall, and the circumferential interior wall defines a diameter that is larger than the diameter defined by the annular upstanding wall.

16. The low-profile cranial device according to claim 15, further including radially extending slots formed along the periphery of the static cranial implant, the slots connecting to an exterior of the static cranial implant at the periphery of the static cranial implant.

17. The low-profile cranial device according to claim 13, wherein the central rotation member holds the electrical lead and controls take-up of the electrical lead.

\* \* \* \* \*